(12) United States Patent
Mercer et al.

(10) Patent No.: US 12,016,641 B2
(45) Date of Patent: Jun. 25, 2024

(54) FLEXIBLE NAVIGATION MARKER SYSTEMS AND METHODS OF USE

(71) Applicant: DePuy Ireland Unlimited Company, Ringaskiddy (IE)

(72) Inventors: Alasdair Mercer, Leeds (GB); Heather Waterson, Warsaw, IN (US); Daren Deffenbaugh, Winona Lake, IN (US); Andrew Bailey, Leeds (GB)

(73) Assignee: DePuy Ireland Unlimited Company, Ringaskiddy (IE)

( * ) Notice: Subject to any disclaimer, the term of this patent is extended or adjusted under 35 U.S.C. 154(b) by 615 days.

(21) Appl. No.: 17/338,330

(22) Filed: Jun. 3, 2021

(65) Prior Publication Data

US 2022/0387112 A1 Dec. 8, 2022

(51) Int. Cl.
*A61B 34/20* (2016.01)
*A61B 90/00* (2016.01)

(52) U.S. Cl.
CPC ...... *A61B 34/20* (2016.02); *A61B 2034/2055* (2016.02); *A61B 2034/2072* (2016.02); *A61B 2090/397* (2016.02)

(58) Field of Classification Search
CPC ............ A61B 34/20; A61B 2034/2055; A61B 2034/2072; A61B 90/39; A61B 2090/397
See application file for complete search history.

(56) References Cited

U.S. PATENT DOCUMENTS

2011/0077510 A1* 3/2011 Moctezuma de la Barrera .......... A61B 34/20
600/426

\* cited by examiner

*Primary Examiner* — Chao Sheng
(74) *Attorney, Agent, or Firm* — Condo Roccia Koptiw LLP

(57) ABSTRACT

A flexible marker system for use with a computer-assisted surgical (CAS) tracking system is disclosed. The system includes a rigid frame or instrument having a plurality of coupling locations each configured to position a navigation marker in a predetermined position and a flexible array configured to be coupled with the rigid frame or instrument. The flexible array can include an elastically deformable body and a plurality of navigation markers, where the flexible array is configured to be coupled to the rigid frame or instrument by stretching the elastically deformable body over the rigid frame or instrument such that each of the plurality of navigation markers is positioned at one of the plurality of coupling locations of the rigid frame or instrument.

31 Claims, 23 Drawing Sheets

FLEXIBLE NAVIGATION MARKER SYSTEMS AND METHODS OF USE

FIELD

This disclosure relates generally to surgical instruments, systems, and methods, and more particularly to devices, systems, and methods for coupling or integrating single-use reflective markers with a reusable chassis or instrument for subsequent use in navigating a surgical robot or instrument during a surgical procedure. Flexible navigational arrays comprising single-use reflective markers and bodies that can be stretched and deformed in order to be attached to a variety of different reusable rigid frames or instruments are disclosed herein.

BACKGROUND

Many different surgical procedures utilize some form of surgical navigation or tracking to aid in positioning surgical instruments relative to portions of patient anatomy during a procedure. One such type of procedure is robotic or robot-assisted surgical procedures, where surgical navigation can be important to correctly position a robotically controlled or assisted surgical instrument relative to a patient.

There are a number of known surgical navigation or tracking technologies, including commonly employed optical navigation or tracking systems that utilize, e.g., stereoscopic sensors to detect infra-red (IR) light reflected or emitted from one or more optical markers affixed to surgical instruments and/or portions of a patient's anatomy. By way of further example, a tracker having a unique constellation or geometric arrangement of reflective elements can be coupled to a surgical instrument and, once detected by stereoscopic sensors, the relative arrangement of the elements in the sensors' field of view, in combination with the known geometric arrangement of the elements, can allow the system to determine a three-dimensional position and orientation of the tracker and, as a result, the instrument or anatomy to which the tracker is coupled.

In known surgical navigation technologies, a navigation array or tracker can be mounted on an instrument that is received and/or controlled by a robotic arm to identify a position of the instrument. In some instances, a navigation array or tracker can be formed integrally with the instrument itself. In other instances, a navigation array can be removably attached to an instrument and can be used to track a position of multiple instruments over the course of a surgical procedure. This approach, however, requires unmounting and remounting of the array with respect to each particular instrument every time a different instrument is used. Both solutions, however, can be inconvenient, as the capability to decouple the array from the instrument or to couple the array to other instruments may be absent or complicated. Further, many types of reflective markers that are used with navigation arrays are fragile and therefore are intended to be single-use devices, and arrangements having the reflective markers integrally-formed in a frame of the array can require the entire navigation array or instrument-array assembly to be single-use, or necessitate the replacement of the entire navigation array or instrument-array assembly if a reflective element is damaged during the operation. This has discouraged the use of robust and reusable navigation arrays that can provide a higher level of accuracy in positioning the reflective markers. Moreover, existing techniques for coupling single-use reflective markers to a navigation array chassis fail to accurately locate the reflective marker relative to the chassis and result in an overall degradation of tracking accuracy.

Accordingly, there is a need for improved systems, methods, and devices for accurately coupling single-use reflective markers with a chassis, which can be a reusable chassis, a single-use chassis, or a chassis integrated with a surgical instrument.

SUMMARY

Certain aspects of the present disclosure provide a coupling system for securing and positioning a single-use flexible navigation marker array to a rigid frame or instrument to form a navigation array suitable for use in computer assisted surgery and similar procedures. A flexible marker system for use with a computer-assisted surgical (CAS) tracking system can include a rigid frame or instrument defining a plurality of coupling locations each configured to position a navigation marker in a predetermined position and a flexible array configured to be coupled with the rigid frame or instrument. The flexible array can include an elastically deformable body and a plurality of navigation markers, where the flexible array is configured to be coupled to the rigid frame or instrument by stretching the elastically deformable body over the rigid frame such that each of the plurality of navigation markers is positioned at one of the plurality of coupling locations of the rigid frame or instrument. Each of the plurality of navigation markers can be rigid and each navigation marker can be configured to be located in space using stereoscopic sensors that detect light reflected or emitted from the navigation markers. In some embodiments, each navigation marker includes an optical lens device configured to reflect infra-red light.

The flexible navigation array can be coupled to a surgical instrument in a variety of manners. For example, a modular rigid frame can be rigidly coupled to a surgical instrument and the flexible navigation array can be coupled to the frame. In other embodiments, a frame can be integrally formed with a surgical instrument such that its position is fixed relative to a body of the instrument and the flexible navigation array can be coupled to the integrally-formed frame. In still other embodiments, an outer surface of a surgical instrument can include coupling locations or features formed directly thereon or therein such that a flexible navigation array can be coupled to the outer surface of the instrument without the use of a frame or frame-like component. For example, a surgical instrument can include recesses formed in an outer surface of the instrument and configured to receive a navigation marker of the flexible array. Such a configuration can potentially reduce cost and complexity while increasing accuracy of tracking by directly coupling the flexible array to a surgical instrument and omitting an intervening rigid frame.

The rigid frame or instrument can include a channel section and a portion of the elastically deformable body can be configured to be received in the channel section when the flexible array is coupled with the rigid frame or instrument. In some embodiments, the channel section defines an end surface and the end surface includes one of the plurality of coupling locations such that an elastic restoration force of the elastically deformable body maintains a position of a navigation marker relative to the end surface when the flexible array is coupled with the rigid frame or instrument. In some embodiments, the rigid frame or instrument includes a plurality of channel sections, each channel section having one of the plurality of coupling locations and a portion of the elastically deformable body can be configured to be received in each of the plurality of channel sections when the flexible array is coupled with the rigid frame or instrument.

The rigid frame or instrument can define a central locating feature, with the elastically deformable body of the flexible array defining a corresponding central locating feature and a plurality of appendages extending therefrom and the central locating feature of the rigid frame or instrument being configured to retain the corresponding central locating feature of the flexible array such that each of the appendages is configured to be held in an elastically deformed configuration extending between the central locating feature of the rigid frame or instrument and a one of the plurality of coupling locations.

The rigid frame or instrument can include a surface with a recess formed therein and defining one of the plurality of coupling locations. At least a portion of the elastically deformable body of the flexible array can be configured to be stretched across the surface when the flexible array is coupled with the rigid frame or instrument.

In some embodiments, the rigid frame or instrument includes a plurality of arms, with each of the plurality of arms including a respective one of the plurality of coupling locations and where a portion of the elastically deformable body is configured to be elastically deformed along each of the plurality of arms when the flexible array is coupled with the rigid frame or instrument. In some embodiments, each of the plurality of arms extends from a central location. In some embodiments, the elastically deformable body includes a plurality of arm sections configured to extend along a corresponding one of the plurality of arms when the flexible array is coupled with the rigid frame or instrument. In some embodiments, at least one of the plurality of arms defines a channel section and the elastically deformable body includes an arm section configured to be received in the channel section when the flexible array is coupled with the rigid frame or instrument. At least one of the coupling locations can include a coupling hook feature and the flexible array can include a loop feature adjacent to a navigation marker that is configured to interface with the coupling hook feature to secure the flexible array to the rigid frame or instrument. In some embodiments, at least one of the coupling locations includes a recess and the flexible array includes a protrusion adjacent to a navigation marker that is configured to be received and retained by the recess when the flexible array is coupled with the rigid frame or instrument.

In some embodiments, at least one of the coupling locations includes a pin and the flexible array includes a strap with holes adjacent to a navigation marker that is configured to be received and retained by the pin when the flexible array is coupled with the rigid frame or instrument. At least one of the coupling locations can include a first pin on a first side of the rigid frame or instrument and a second pin on a second side of the rigid frame or instrument opposite the first side, and the flexible array can include first and second strap portions with a navigation marker disposed between the first and second strap portions, with the first and second strap portions each defining one or more holes configured to receive the first and second pins, respectively, when the flexible array is coupled with the rigid frame or instrument. At least one of the coupling locations can define a curved surface, and the flexible array can include a first side having a navigation marker and a second side, opposite the first side, configured to interface with the curved surface of the coupling location when the flexible array is coupled with the rigid frame or instrument.

Another example of the present disclosure is flexible marker for use with a computer-assisted surgical (CAS) tracking system that includes an elastically deformable flexible body and a plurality of rigid navigation markers configured to be detected by a CAS tracking system, with the elastically deformable flexible body being configured to be stretched over a rigid frame or instrument in order to position the plurality of rigid navigation markers at specific positions relative to the rigid frame or instrument. In some embodiments, each of the plurality of rigid navigation markers includes a rigid hemisphere portion. In some embodiments, each of the plurality of rigid navigation markers is configured to reflect infra-red light. In some embodiments, the elastically deformable flexible body has a plurality of appendages, each containing one of the plurality of rigid navigation markers. In some embodiments, the plurality of rigid navigation markers includes at least three markers. In some embodiments, the plurality of rigid navigation markers includes at least four markers. In some embodiments, the plurality of rigid navigation markers includes at least one more marker than is required for operation of a CAS tracking system.

Yet another example is a surgical method that includes positioning a rigid frame or instrument relative to an object to be tracked by a CAS system and elastically deforming a body of a flexible array over the rigid frame or instrument and positioning a plurality of navigation markers of the flexible array at coupling locations of the rigid frame or instrument. In some embodiments, the method includes elastically deforming a first strap of the body and coupling the first strap to a retention feature on a first side of the rigid frame or instrument. In some embodiments, the method includes elastically deforming a second strap of the body and coupling the second strap to a retention feature on a second side of the rigid frame or instrument. In some embodiments, disposing a portion of the body in a channel of the rigid frame or instrument such that a coupling region at an end of the channel secures one of the plurality of navigation markers and retains the body in an elastically deformed position. Each navigation marker can include an optical lens device configured to reflect infra-red light. And elastically deforming a body of the flexible array can include elastically deforming a plurality of appendages of the body, each containing one of the plurality of rigid navigation markers. In some embodiments, the method can further include any of removing or hiding from view at least one of the navigation markers of the flexible array, e.g., by cutting away at least one of the navigation markers or tucking at least one of the navigation markers behind another portion of the flexible array to hide it from view of the CAS tracking system.

Another example of a flexible marker system for use with a CAS tracking system includes a rigid frame or instrument defining a plurality of coupling locations and a flexible array configured to be coupled with the rigid frame or instrument. Each of the plurality of coupling locations can be configured to position a respective navigation marker in a predetermined spatial position with respect to the other coupling locations and the flexible array can have a body defining at least three flexible regions, with each of the at least three flexible regions defining a coupling region carrying a navigation marker. Each coupling region of the flexible array can be configured to interface with one of the plurality of coupling locations of the rigid frame or instrument when the flexible array is coupled with the rigid frame or instrument and each of the least three flexible regions can be configured to be held in an elastically deformed configuration by the rigid frame to locate a respective navigation marker in a respective one of the plurality of coupling locations. Additionally, the flexible array can be configured to be coupled with the rigid frame or instrument when each of the at least three flexible regions are held in the elastically deformed configuration by the rigid frame or instrument such that each of the navigation markers is located in the respective coupling location of the rigid frame or instrument. Each navigation marker can be configured to be located in space using stereoscopic sensors that detect light reflected or emitted from the navigation markers. In some embodiments, each navigation marker includes an optical lens device configured to reflect infra-red light.

The rigid frame or instrument can include a channel section and at least one of the flexible regions can include an arm section sized and shaped to be received in the channel section when the flexible array is coupled with the rigid frame or instrument. In some embodiments, the channel section defines an end surface and the end surface includes one of the plurality of coupling locations, the end surface being configured to abut or contact a surface of the coupling region such that an elastic restoration force of the respective arm section of the flexible region maintains the position of the coupling region in a the predetermined spatial position when the flexible array is coupled with the rigid frame or instrument.

The rigid frame or instrument can include a plurality of channel sections, each channel section having one of the plurality of coupling locations, and each of the least three flexible regions can include an arm section sized and shaped to be received in one of the plurality of channel sections when the flexible array is coupled with the rigid frame or instrument.

The rigid frame or instrument can include a central locating feature, with the body of the flexible array defining a corresponding central locating feature and the central locating feature being configured to retain the corresponding central locating feature of the flexible array such that each of the flexible regions is configured to be held in the elastically deformed configuration by being deformed between the central locating and a respective one of the plurality of coupling locations.

In some embodiments, the rigid frame or instrument includes a surface, the surface having formed therein a recess defining one of the plurality of coupling locations and at least a portion of the flexible array is configured to be stretched across the surface when the flexible array is coupled with the rigid frame or instrument. In some embodiments, the rigid frame or instrument includes a plurality of arms, with each of the plurality of arms including a respective one of the plurality of coupling locations, and each of the least three flexible regions being configured to be elastically deformed along a respective one of the plurality of arms when the flexible array is coupled with the rigid frame or instrument. In some embodiments, each of the plurality of arms extends from a central location. In some embodiments, each of the least three flexible regions includes an arm section sized and shaped to extend along a corresponding one of the plurality of arms when the flexible array is coupled with the rigid frame or instrument. In some embodiments, at least one of the plurality of arms defines channel section and at least one of the flexible regions includes an arm section sized and shaped to be received in the channel section when the flexible array is coupled with the rigid frame or instrument.

In some embodiments, the body of the flexible array defines a relaxed shape when each of the at least three flexible regions is not elastically deformed and each of the at least three flexible regions is configured to elastically deform to change a spatial dimension of the body to enable each of the three navigation markers to be moved to a different one of the predetermined spatial positions of the rigid frame or instrument. The flexible array can be configured to be coupled to the rigid frame or instrument when each of the coupling regions of the flexible array are secured to the coupling locations and when each of the three navigation markers is in a different one of the predetermined spatial positions of the rigid frame or instrument. In some embodiments, each of the coupling locations of the rigid frame or instrument is configured to retain a coupling region of the flexible body to couple the flexible array to the rigid frame or instrument.

In some embodiments, at least one of the coupling locations includes a coupling hook feature, and at least one of the coupling regions of the flexible array includes a loop feature configured to be elastically deformed and attached to the coupling hook feature to secure the flexible array to the rigid frame or instrument. At least one of the coupling locations can includes a recess and at least one of the coupling regions of the flexible array can include a protrusion configured to be received and retained by the recess when the flexible array is coupled with the rigid frame or instrument. In some embodiments, at least one of the coupling locations includes a pin, and at least one of the coupling regions of the flexible array includes a strap with holes configured to be received and retained by the pin when the flexible array is coupled with the rigid frame or instrument.

At least one of the coupling locations can include a first pin on a first side of the rigid frame or instrument and a second pin on a second opposite side of the rigid frame or instrument, where at least one of the coupling regions defines regions includes first and second strap portions with the navigation marker disposed along a length of the coupling region and between the first and second strap portions, and the first and second strap portions each define one or more holes configured to be received and retained by the first and second pins, respectively, when the flexible array is coupled with the rigid frame or instrument.

In some embodiments, at least one of the coupling locations can define a curved surface, and at least one of the coupling regions can define a first side having the navigation marker and a second side, opposite the first side, configured to be received and positioned by the curved surface of the coupling location when the flexible array is coupled with the rigid frame or instrument.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF DRAWINGS

This disclosure will be more fully understood from the following detailed description taken in conjunction with the accompanying drawings, in which.

DETAILED DESCRIPTION

Figure 1:
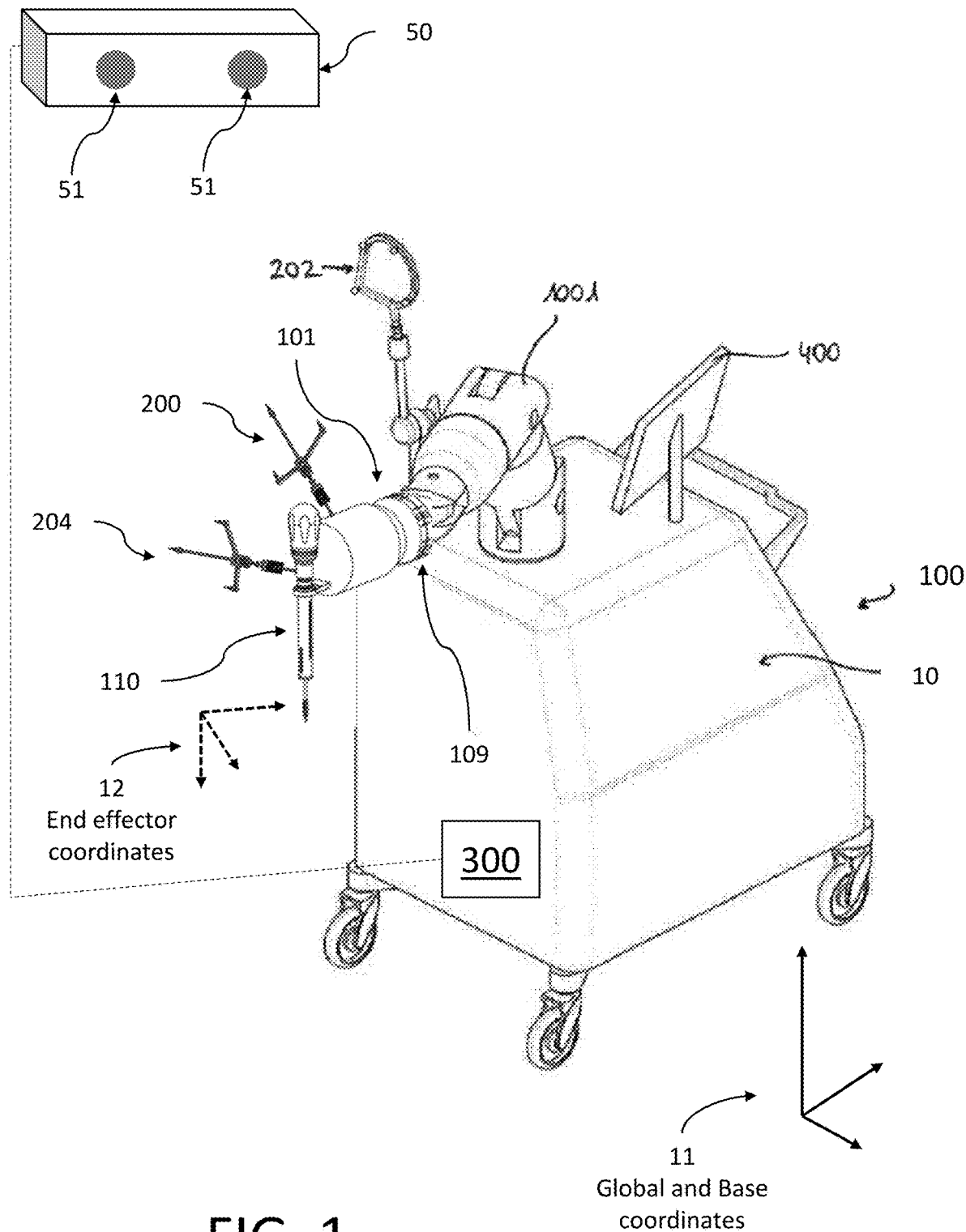
FIG. 1 is a schematic of a surgical robot with an attached end effector and a surgical navigation marker array disposed on the surgical robot for use in tracking the position of the distal end of the surgical robot and end effector.

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting example embodiments and the scope of the present disclosure is defined solely by the claims. The features illustrated or described in connection with one embodiment may be combined with the features of other embodiments. Such modifications and variations are intended to be included within the scope of the present disclosure.

Additionally, to the extent that linear or circular dimensions are used in the description of the disclosed devices, systems, and methods, such dimensions are not intended to limit the types of shapes that can be used in conjunction with such systems and methods. Equivalents to such linear and circular dimensions can be determined for any geometric shape. Further, in the present disclosure, like-numbered components of the embodiments generally have similar features. Still further, sizes and shapes of instruments or systems, and the components thereof, can depend at least on the anatomy of a subject with which the instruments or systems will be used, the size and shape of other components with which the instruments or systems will be used, and the methods and procedures in which the instruments or systems will be used.

Devices, systems, and methods for coupling navigation markers to surgical navigation arrays are disclosed herein, e.g., using a flexible array carrying a navigation marker and a rigid frame or instrument for holding the flexible array and making it conform to a predetermined geometric shape defined by the rigid frame or instrument.

In some embodiments, a flexible navigation array can include a plurality of rigid navigation makers disposed therein and a plurality of coupling regions or elements that are arranged to be secured to a rigid frame or instrument. The body of the flexible navigation array can include a plurality of arms, with each having a navigation marker such that the arms can be stretched and deformed to position the flexible navigation array on a variety of different sizes and shapes of rigid frames or instruments. The flexible navigation array and navigation markers can be made as a single use part to be used with reusable rigid frames or instruments. This configuration can have a number of advantages. For example, navigation makers are often designed to be single use parts due to, for example, their low tolerances for sterilization and their fragile nature (e.g., a surgical tracking system can be sensitive to defects in the reflective character of a navigation marker, which encourages using new markers for each procedure), but surgical navigation arrays need to position the navigation markers with very high spatial tolerances, both with respect to each other and to whatever element the navigation array is attached to, which encourages robust and rigid navigation arrays. Together, these two competing design directions (i.e., fragile navigation markers and robust arrays) can be separately solved by aspects of the present disclosure, which separate the navigation array into two separate components: (1) a rigid frame or instrument that can be reusable, highly tolerant to sterilization, and able to provide accurate locations for navigation markers, and (2) a flexible navigation array, which can be single use and hold a plurality of navigation makers in a body that can be deformed and attached to a variety of rigid frames, while also using the deformable nature of the body to ensure accurate placement of the navigation makers with respect to the rigid frame by accounting for the restoration force of the body holding the flexible array in a stable arrangement when secured to the rigid frame. Additionally, the arms of the rigid body can include one or more exterior features for securing the flexible navigation array to the rigid body. In some examples, the navigation marker can be a reflective marker that includes a lens element and a reflective element visible through the lens element, e.g., a hemispherical or spherical clear lens with a reflective surface or reflective element configured to be visible through the lens element.

In operation, the navigation array with a carrier frame and navigation markers disposed therein can be coupled to a surgical robotic arm or other instrument and can be configured to locate an absolute position of the robotic arm or instrument in three-dimensional space, such as the distal end of the robotic arm where a tool end effector is present. For example, a navigation array can be mounted on a tool end effector (e.g., directly onto a tool carried by a tool holder or on the tool holder) and can be configured to locate a position of the tool end effector based on a position of the array. In this manner, the array can precisely track a spatial parameter, such as distance, depth, or orientation, of a distal end of the tool end effector without any additional sensors or encoders present on the robotic arm. As such, a need to provide electronics in each instrument or instrument mount used throughout a surgical procedure can be eliminated. Accordingly, the navigation arrays of the present disclosure can locate absolute placement of the robotic arm and associated or other instrumentation during the course of a surgical procedure in an effective and efficient manner without disrupting surgical flow or requiring excessive handling of instrumentation.

FIG. 1 illustrates embodiments of computer-assisted surgical (CAS) systems that can be utilized with the systems and methods described herein. Such systems can utilize any of surgical navigation/tracking and robot control or assistance to monitor or control movement of one or more surgical instruments during a procedure. While the illustrated embodiments and accompanying description do not make particular reference to a specific surgery, the systems and methods described herein can be utilized in various applications involving robotic, robot-assisted, and non-robotic operations where computer-assisted tool location are required and precise adjustment of tool position may be appropriate. Example applications include knee surgery, e.g., total knee arthroplasty (TKA) or unicompartmental knee arthroplasty (UKA), hip surgery, e.g., hip arthroplasty, shoulder surgery, spine surgery, etc. The teachings of the present disclosure can be applied to such procedures; however, the systems and methods described herein are not limited to these applications.

FIG. 1 shows an overview of a surgical system according to the present disclosure. In FIG. 1 a robotic device 100, including a surgical robot arm 1001, that includes an attached tool end effector 110 and a plurality of arm segments 101 connected by rotatable or otherwise articulating joints 109. A distal-most segment can include a navigation array 200 mounted thereto and terminates at distal end with the tool end effector 110. FIG. 1 also shows a global coordinate system 11 of the robotic device 100 and an end effector coordinate system 12 of the tool end effector. The global coordinate system 12 can be defined in different ways and, in some embodiments, can use the location of a base 10 of the robotic device 110, which may or may not itself be stationary, as an origin. The location of the distal-most arm segment of the robotic device can be calculated by receiving a position signal from an encoder in each joint 109 and/or by measuring a position of the navigation array 200 to directly detect the position of the arm segment and determine the position of the distal end thereof in the global coordinate system 11. In some instances, a measured coordinate system of the navigation array 200 can be different from the global coordinate system 11 and calculations can be utilized to harmonize the two coordinate systems. In some embodiments, the measured coordinate system can be used as the global coordinate system 11. The end effector coordinate system 12 can be defined in different ways but can refer to the position and orientation of the tool end effector 110 with respect to the operation of the tool end effector (e.g., if the tool end effector includes a cutting bit, the cutting direction can be along an "up" or "down" axis that might be defined by, e.g., a longitudinal axis of the tool). The tool end effector 110 held by the robotic device 100 can be constrained to move about the distal end of the distal-most arm segment such that the summation of the positions of joints 109 can define the location of the an end effector coordinate system 12 in the global coordinate system 11 with respect to a control system of the joints 109 to control movement of the tool end effector 110. Accordingly, the robotic device 100 can be connected to a control unit 300 that controls the actuation of each joint 109 in order to position the tool end effector 110. The control unit 300 typically comprises power supply, AC/DC converters, motion controllers, and other components to power the motors of the actuation units in each joint 109, as well as fuses, real-time control system interface circuits, and other components conventionally included in surgical robot devices. As noted above, the description provided herein makes reference to the surgical system shown in FIG. 1, but the present disclosure is also contemplated for use with any surgical device, for example, a saw blade, burr, reamer, mill, knife, or any other implement that could cut or deform bone and is appropriate for use in a given operation. Further, the present disclosure is also contemplated to include use of such instruments by surgical robots, by users with some degree of robotic assistance, and without involvement of surgical robots or robotic assistance (e.g., where solely surgical navigation/tracking is utilized).

Further, in some embodiments additional and/or alternative navigation arrays can be employed in addition to, or in place of, the navigation array 200 shown attached to a distal-most arm segment 101 of the robotic arm 1001. For example, in some embodiments a navigation array 202 can be coupled to another component of the robotic device, such as a base of the robotic arm 1001 in embodiments where the robot is mobile. Still further, a navigation array 204 can be coupled to the tool end effector itself. In embodiments where a single tool is provided, the array 204 can be coupled directly thereto. In other embodiments, however, the tool end effector 110 can be a cannula or guide configured to receive one or more surgical instruments. In such embodiments, the navigation array 204 can be coupled to the cannula or guide and positioning of an instrument inserted therethrough can be achieved using a different array or different tracking means.

Returning to the system illustrated in FIG. 1, the system also comprises a tracking unit 50, such that the relative pose or three-dimensional position and orientation of the navigation array 200 (and/or other navigation arrays) can be tracked in real time and shared to the control unit 300 and any additional planning or control system. In some instances, coordinate systems can be attached to the robotic device 100 via the navigation array 200, the end effector 110 via a tool array (e.g., array 204), and an anatomical structure (not shown). The tracking unit 50 can measure the relative motions between any and all coordinate systems in real time. Real time can, in some embodiments, mean high frequencies greater than twenty Hertz, in some embodiments in the range of one hundred to five hundred Hertz, with low latency, in some embodiments less than five milliseconds.

Figure 2A:
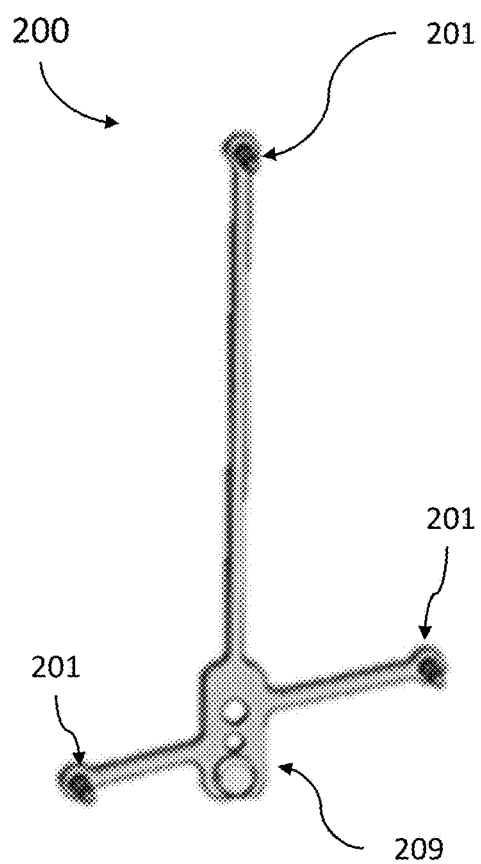
FIG. 2A is a perspective-view illustration of an example surgical navigation array having three markers and configured to locate an attachment point in three-dimensional space by a navigation system.
Figure 2B:
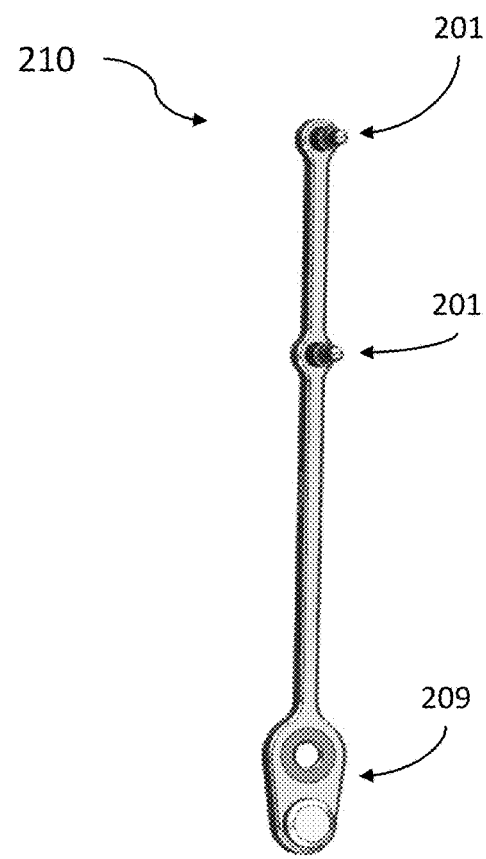
FIG. 2B is a perspective-view illustration of a navigation arraying having two markers and configured to locate axis of an attachment point in three-dimensional space.

FIGS. 2A and 2B show example conventional navigation arrays for use with the tracking unit 50. FIG. 2A is an illustration of a navigation array 200 having three markers and configured locate an attachment point in three-dimensional space by a navigation system. FIG. 2B is an illustration of a navigation array 210 having two markers and configured to locate an axis of an attachment point in three-dimensional space. The navigation arrays 200, 210 utilize any of a variety of trackers and tracking technologies known for use in surgical navigation. These can include, for example, optical trackers consisting of reflective or active markers detected by a sensor 51 (shown as part of the tracking unit 50 in FIG. 1) disposed inside or in view of the surgical field. In the illustrated embodiments, for example, the tracking unit 50 can include a passive optical tracker consisting of, for example, a constellation of reflective tracking elements 201 having a fixed geometric relationship that can be coupled to a portion of patient anatomy, a surgical instrument, or other component to be tracked. The tracking unit 50 can include a stereoscopic sensor having two or more physically separated detectors 51 that can be used to detect light reflected off each of the tracking elements (e.g., reflected infra-red (IR) light in some embodiments). The sensor 51, in some embodiments in conjunction with other information processing components such as the control unit 300, can utilize the known fixed geometric relationship between the tracking elements 201, a mounting point 209, and the detected positions of the tracking elements in the fields of view of the two detectors 51 to determine a precise three-dimensional position and orientation of the navigation array 200, 210 (and therefore of the anatomy, tool, or robotic segment coupled via the mounting point 209) within the surgical field.

In some embodiments, however, other types of surgical navigation and tracking can be employed in place of, or in addition to, the above-described reflective optical tracking. For example, in some embodiments optical tracking can be employed using active light emitters rather than reflective elements, such as light emitting diodes (LEDs). In other embodiments, electromagnetic trackers can be employed, while in still other embodiments any of inertial sensors using gyroscopic measurements, ultrasonic sensors, radio-frequency identification (RFID) sensors, or other known sensors can be employed.

Regardless of how it is gathered, position and orientation data can be transferred between components (e.g., to the control unit 300) via any suitable connection, e.g., with wires or wirelessly using a low latency transfer protocol. The real-time control unit 300 can carry out real-time control algorithms at a reasonably high frequency with low additional latency to coordinate movement of the robotic device 100.

Prior navigation arrays like those shown in FIGS. 2A and 2B can have drawbacks, however. For example, when utilizing optical reflective markers as described above, manufacturers or users are required to couple the reflective markers to the plurality of tracking element posts 201. This can be done by adhesive, ultrasonic welding, interference fit, etc. The reflective markers, however, are fragile and can be easily damaged during use, in some cases even by simple exposure to fluids in the surgical field. As a result, an array with non-removably attached markers may have to be discarded after a single use, even if the frame might be suitable for cleaning, sterilization, and re-use.

Figure 3A:
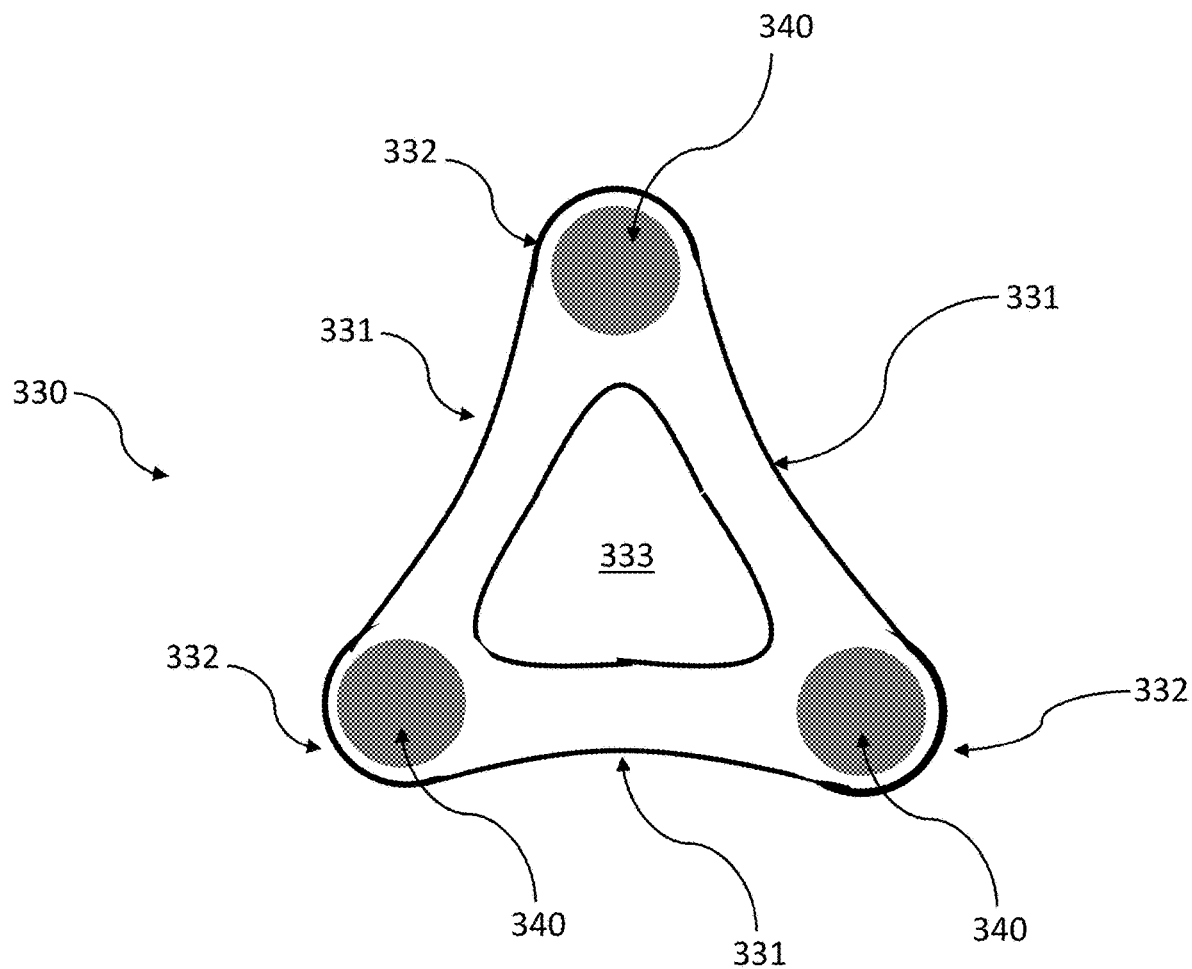
FIG. 3A is a top-view illustration of an embodiment of a flexible navigation array.
Figure 3B:
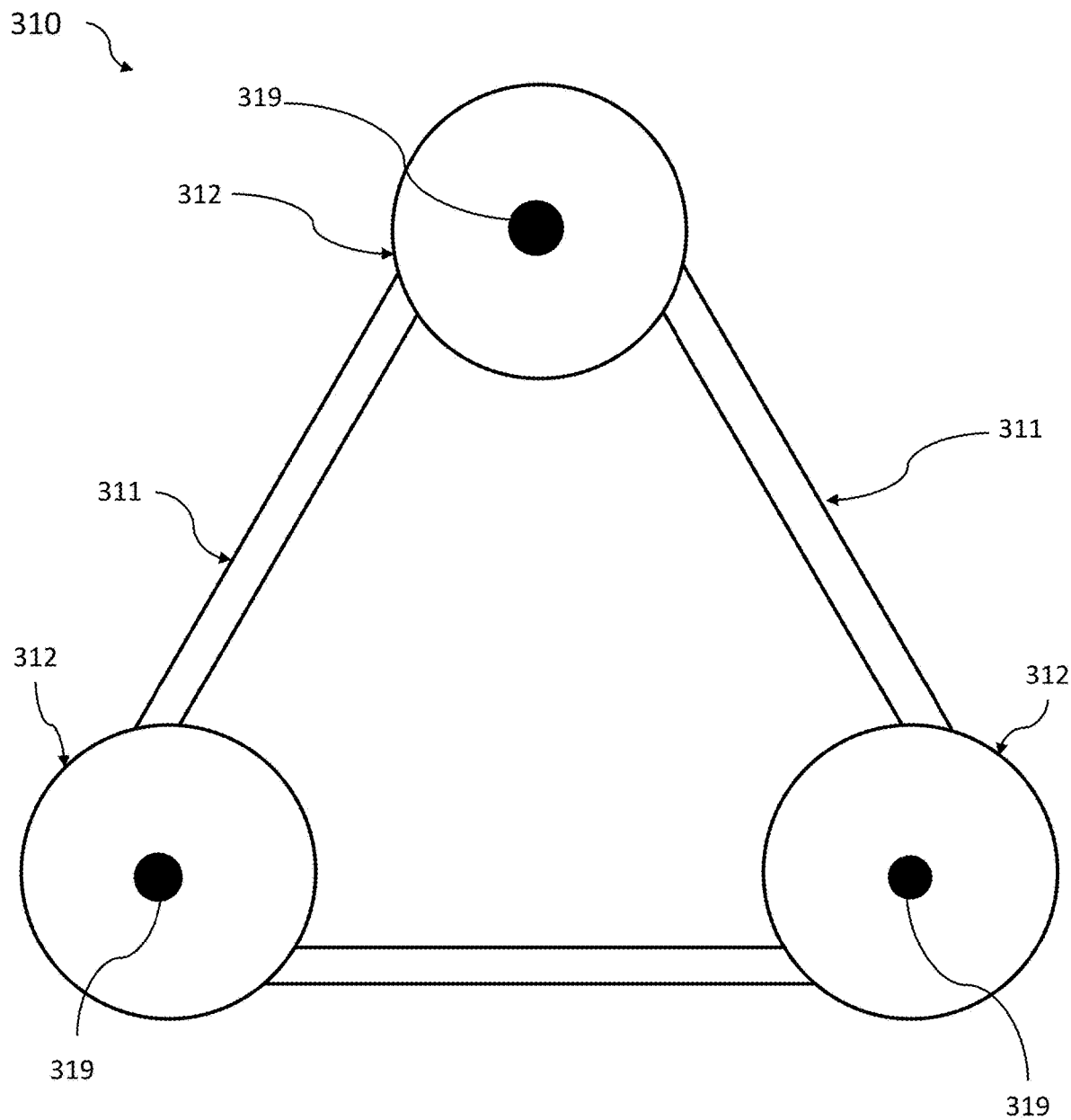
FIG. 3B is a top-view illustration of an embodiment of a rigid frame for holding a flexible navigation array.

FIG. 3A is an illustration of one embodiment of a flexible navigation array 330 that includes a body having a triangular shape defined by three arms 331 and a central opening 333. Each of the three arms 331 extends between a coupling region 332 that carries a rigid navigation marker 340. At least a portion of the arms 331, and, in some embodiments, up to the entire arms 331, entire body, and coupling regions 332, are constructed from a flexible, stretchable, and/or deformable material such that the shape, size, and orientation of the flexible navigation array 330 can be changed in order to couple the flexible navigation array 330 to a rigid frame or instrument of a given size and orientation, for example, as shown in FIG. 3B with regard to the rigid frame 310. Returning to FIG. 3A, the rigid navigation markers 340 can include, for example, housings carrying a lens and reflective element in order to be tracked be a surgical navigation system.

The flexible navigation array 330 can be formed from a variety of materials, and in some cases from multiple materials. For example, the flexible arms 331 can be formed from a lower durometer shore hardness polymer such as a silicon, rubber, or other polymer, and the rigid navigation markers 340 can be formed from a higher durometer shore hardness materials, such as glass, polycarbonate, etc. The flexible navigation array 330 can be a single use component in some embodiments, while in other embodiments can be suitable for cleaning and certain types of sterilization, such as gamma radiation.

FIG. 3B is an illustration of an embodiment of a rigid frame 310 for holding a flexible navigation array 330. The rigid frame 310 includes a plurality of coupling locations 312 configured to receive the coupling regions 332 of the flexible navigation array 330 secured thereto. The coupling regions 332 can include a coupling feature 319, such as a pin, recess, or other means for retaining the coupling regions 332 of the flexible navigation array 330 in the coupling location 312 of the frame 310. Each of the coupling locations 312 is connected by an arm 311 that defines the overall shape and size of the rigid frame 310.

The rigid frame 310 can be formed from a variety of materials having a higher durometer shore hardness, including metals such as aluminum, titanium, and stainless steel, or a variety of engineered polymers. The rigid navigation array can be a single use component in some embodiments, but in many cases can be suitable for re-use following cleaning and sterilization by chemical wash, steam, etc.

Figure 3C:
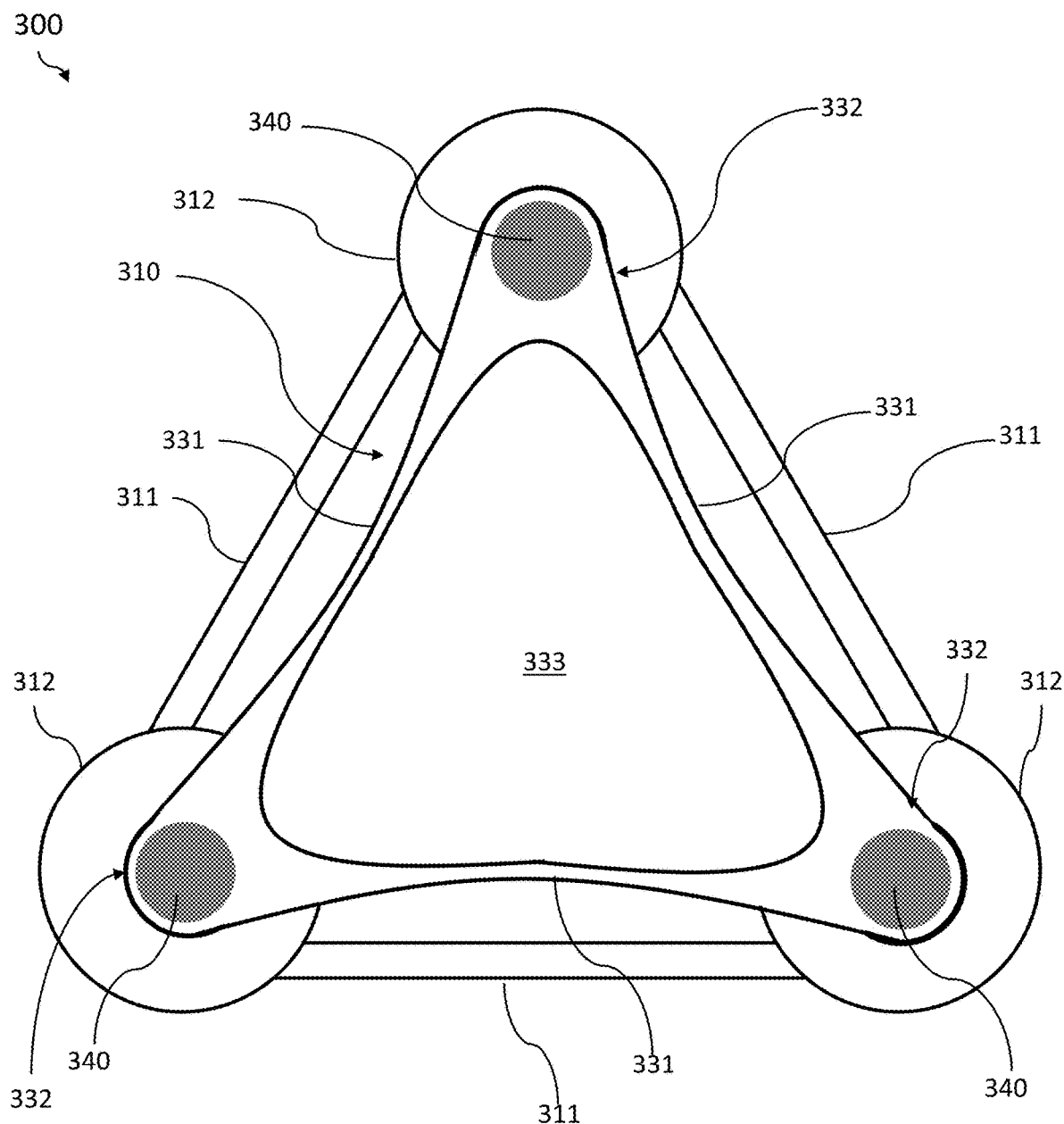
FIG. 3C is a top-view illustration of the flexible navigation array embodiment of FIG. 3A coupled with the rigid frame embodiment of FIG. 3B.

FIG. 3C is an illustration of a surgical navigation tracker 300 that includes the flexible navigation array 330 coupled with the rigid frame 310. Each of the coupling regions 332 of the flexible navigation array 330 is secured to a corresponding one of the coupling locations 312 of the rigid frame 310 via the coupling feature 319 such that each of the rigid navigation markers 340 are positioned in the coupling location 312 and the arms 331 of the flexible navigation array 330 are stretched in order to deform the overall size of the flexible navigation array 330 to match the rigid frame 310.

Figure 4:
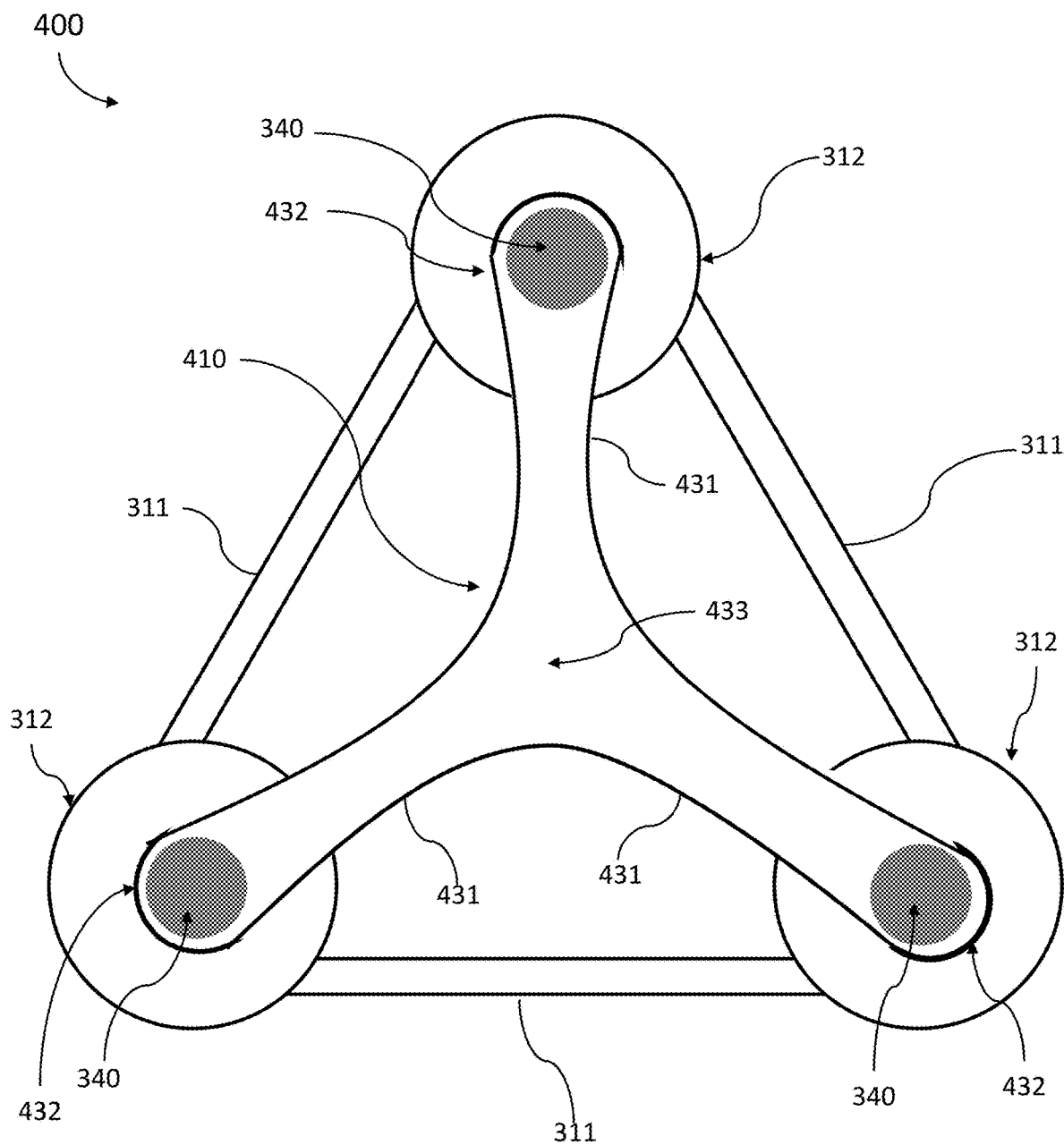
FIG. 4 is a top-view illustration of another flexible navigation array embodiment coupled with the rigid frame embodiment of FIG. 3B.

As mentioned above, the flexible navigation array 330 can be coupled with rigid frames of many different shapes and sizes. Additionally, different flexible navigation array sizes and shapes are possible and can be coupled with the rigid frame 300. For example, FIG. 4 is an illustration of another flexible navigation array 410 that is coupled with the rigid frame embodiment of FIG. 3B to form a surgical navigation array 400. The flexible navigation array 410 includes three coupling regions 432, each carrying a rigid navigation marker 340 and being connected by an arm 431, with each arm 431 extending from a central region 433 of the body of the flexible navigation array 410. Each coupling region 432 is secured to the coupling location 312 of the rigid frame 310 via the coupling feature 319 to position the respective rigid navigation marker 340 in the coupling location 312. In operation, the retention of the coupling region 432 to the coupling location 312 holds the arms 431 of the flexible navigation array 410 in a stable deformed position, e.g., resisting any restoring force of the deformable material of the arms 431.

Figure 5A:
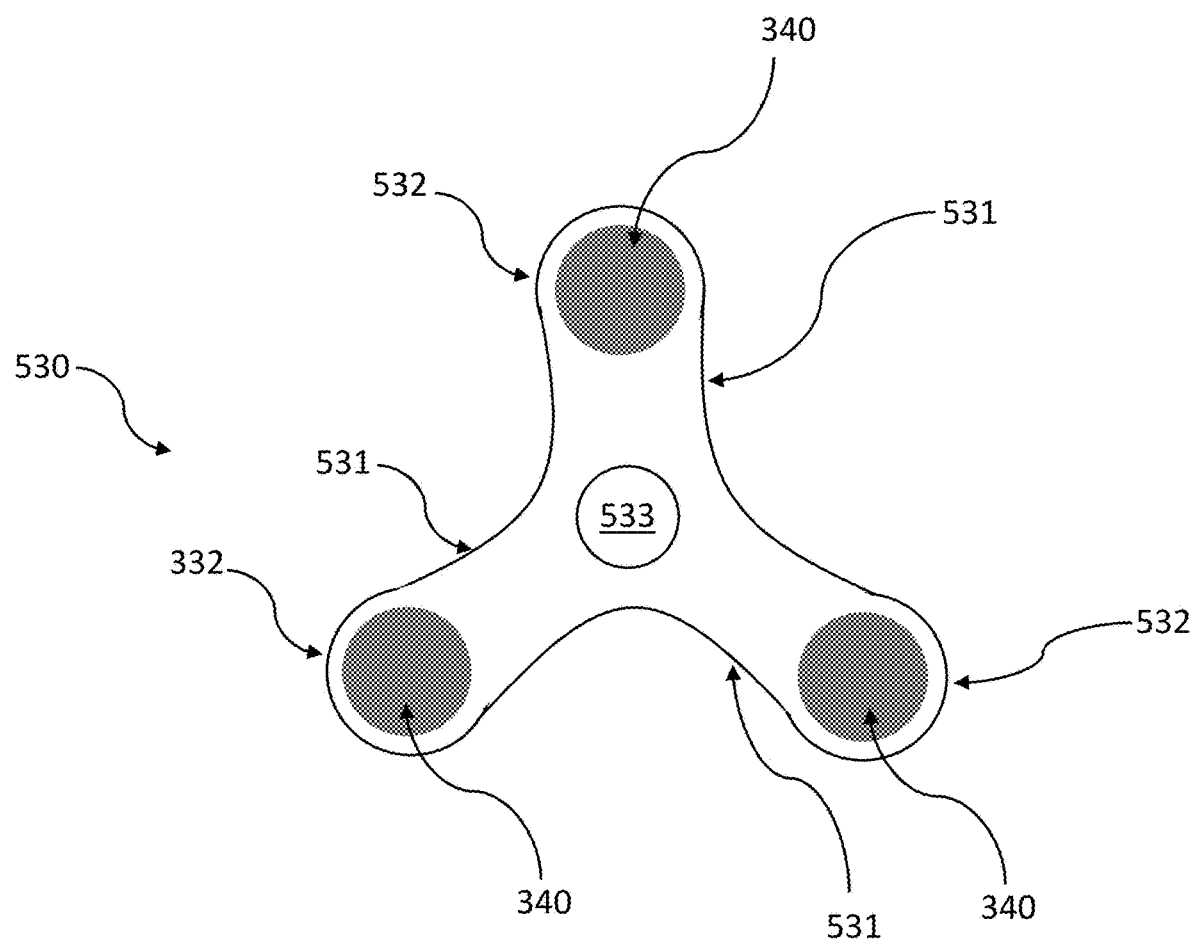
FIGS. 5A and 5B are top-view illustrations of another embodiment of a flexible navigation array.
Figure 5B:
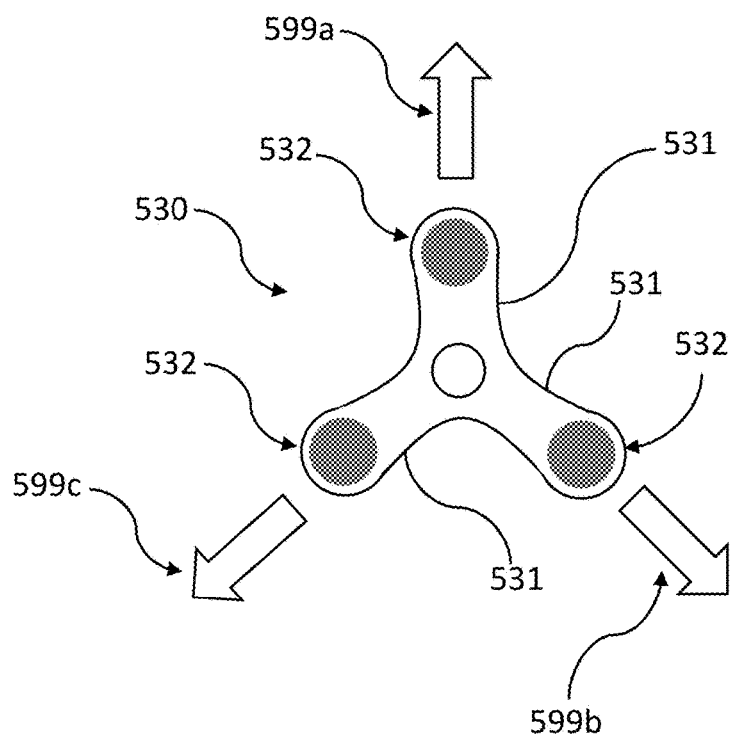

FIGS. 5A and 5B are illustrations of another embodiment of a flexible navigation array 530. The flexible navigation array 530 includes a body having three arms 531 each centrally connected at one end around a central opening 533 and to a coupling region 532 at an opposite end, with the coupling region 532 carrying a rigid navigation marker 340. At least a portion of each arm 531 is deformable and up to the entire body can be made from one or more deformable materials such that the size and shape of the flexible navigation array 530 can be stretched to fit the flexible navigation array 530 onto a variety of different shaped rigid frames or instruments. Additionally, the central opening 533 can further help locate the flexible navigation array 530 on a rigid frame or instrument and provide an anchor point for the arms 531 to pull against when, for example, the central opening 533 is disposed around a protruding feature of the rigid frame or instrument, such as a peg. FIG. 5B shows the flexible navigation array 530 being deformed for attachment onto a rigid frame or instrument. Each arm 531 is pulled in a different direction 599a-599c in order to move each coupling region 532 to a corresponding attachment location on a rigid frame or instrument. In some instances, the flexible navigation array 530 is first attached to a rigid frame or instrument, for example, by coupling the central opening 533 to a corresponding attachment point (e.g., a peg 513) and then deforming the body of the flexible navigation array 530 with the central opening 533 fixed in position. In this manner, the central opening 533, when secured, can allow each arm 531 to be deformed independently of the others.

Figure 5C:
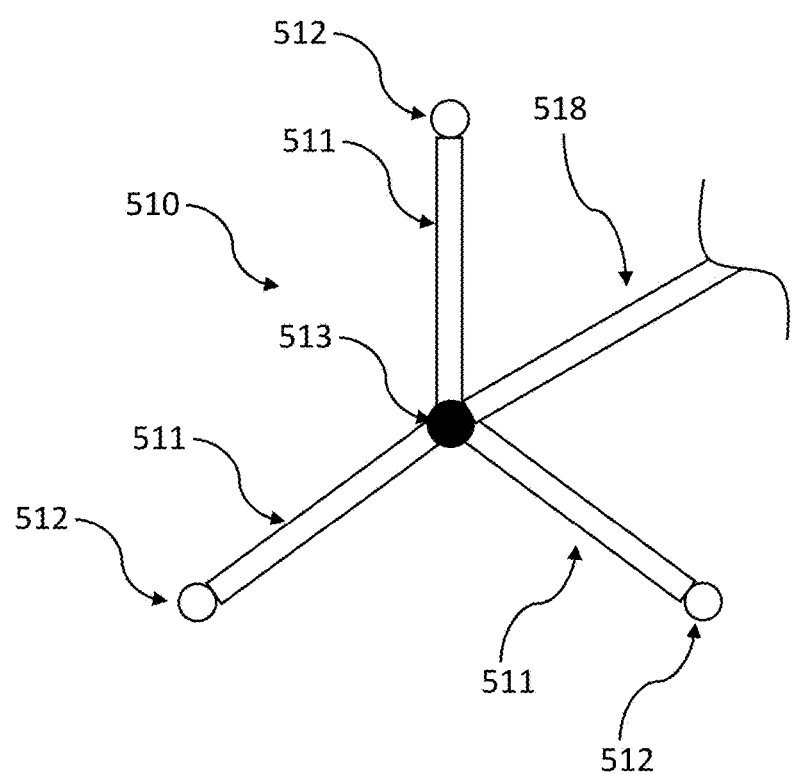
FIG. 5C is a top-view illustration of an embodiment of another rigid frame for holding a flexible navigation array.

FIG. 5C is an illustration of an embodiment of a rigid 510 frame for holding a flexible navigation array 500. The rigid frame 510 includes a plurality of arms 511 each extending from a central location with a central attachment peg 513 (e.g., that extends out of the plane of the page in the top-view figure) to a coupling location 512. The rigid frame also has an attachment arm 518 for securing the rigid frame 510 to, for example, a tool or surgical robot. In operation, and as discussed above with respect to FIG. 5B, the central opening 533 of the flexible navigation array 530 can first be secured to the central attachment peg 513 and then each arm 531 of the flexible navigation array 530 can be deformed in order to bring each coupling region 532 to the coupling location 512 of the rigid frame, where it can be securely attached. Once all of the coupling regions 532 are attached to the coupling locations 512, the flexible navigation array 530 can be securely fastened to and held in a deformed position by the rigid frame 510, as shown in FIG. 5D.

Figure 5D:
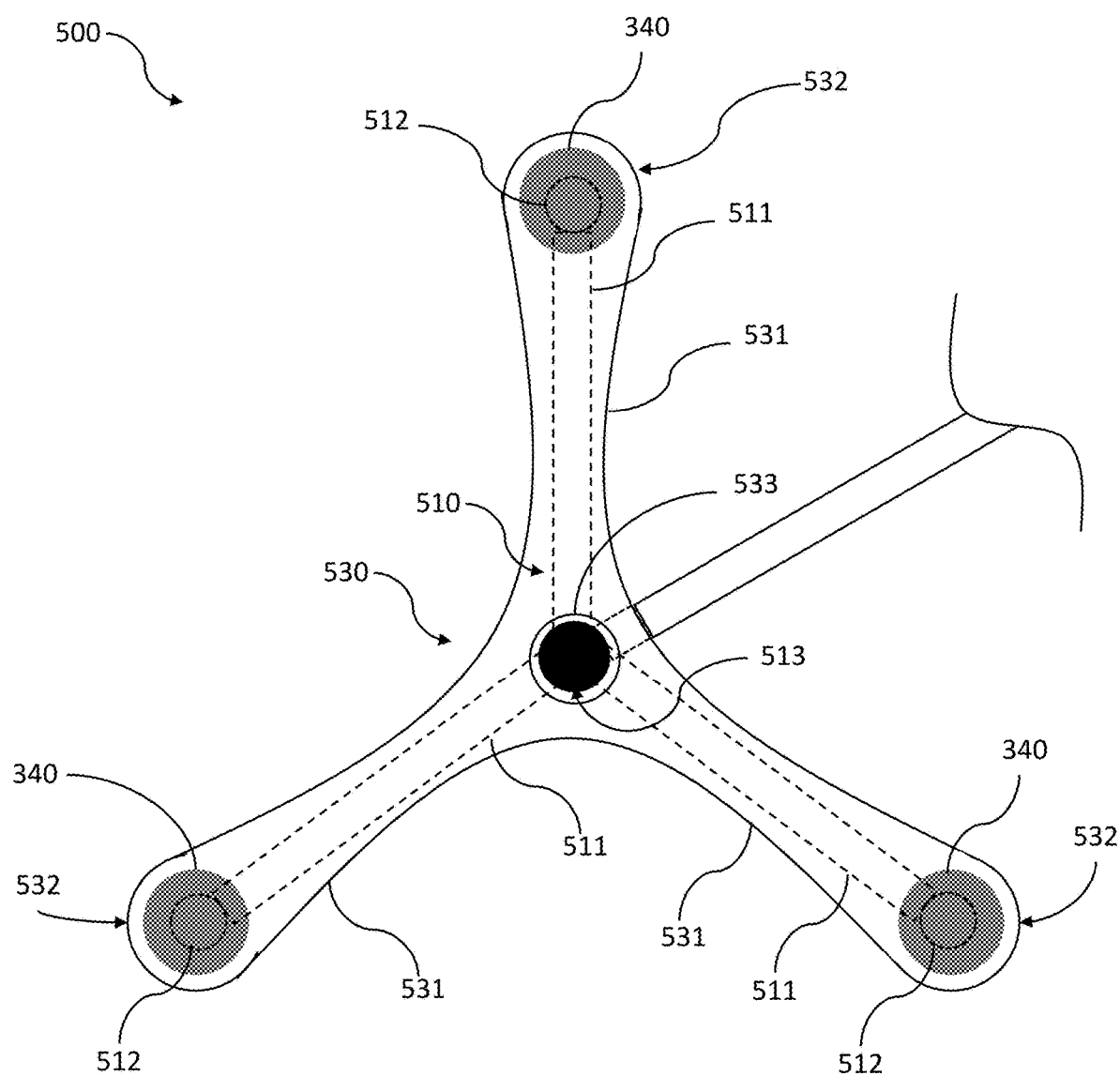
FIGS. 5D and 5E are top-view illustrations of the flexible navigation array embodiment of FIG. 5A coupled with the rigid frame embodiment of FIG. 5C.
Figure 5E:
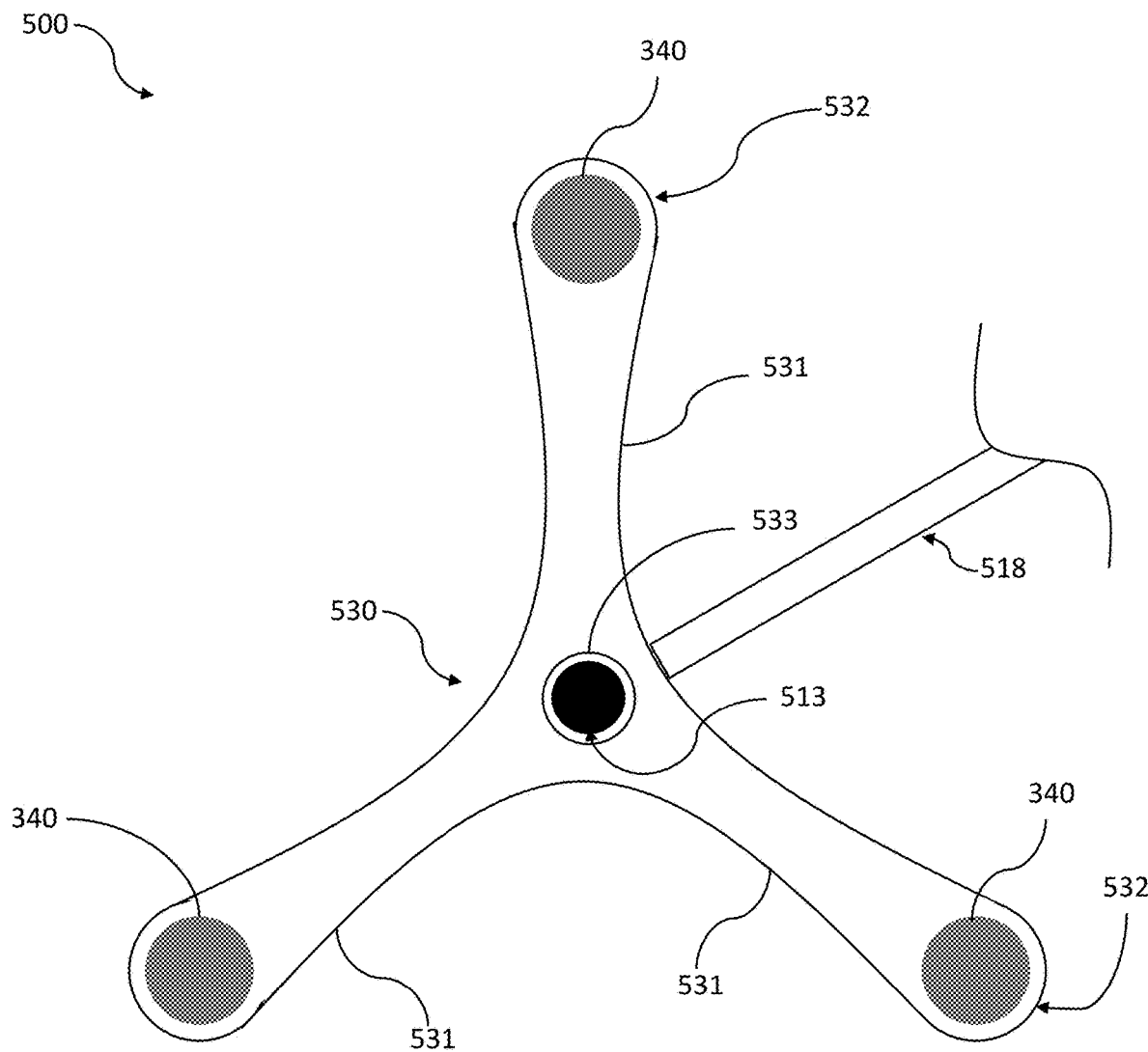

FIGS. 5D and 5E are illustrations of the flexible navigation array 530 coupled with the rigid frame 510 to form a surgical navigation array 500. FIG. 5D shows the flexible navigation array 530 deformed such that each arm 531 is stretched between the central opening 533 and a respective coupling location 512. The central opening 533 of the flexible navigation array 530 is disposed around the central attachment peg 513 of the rigid frame and each coupling region 532 of the flexible navigation array 530 is secured to a respective coupling location of the rigid frame 510. In FIG. 5D, arms 511 of the rigid frame 510 are shown with dotted lines to indicate that they are behind or below the arms 531 of the flexible navigation array 530 and in FIG. 5E the arms 511 are not visible, such that FIG. 5E illustrates how the surgical navigation array 500 appears (from the top-view perspective) to a surgical tracking system during use, with the rigid navigation markers 340 visible and located as the precise positions determined by the coupling locations 512.

Figure 12A:
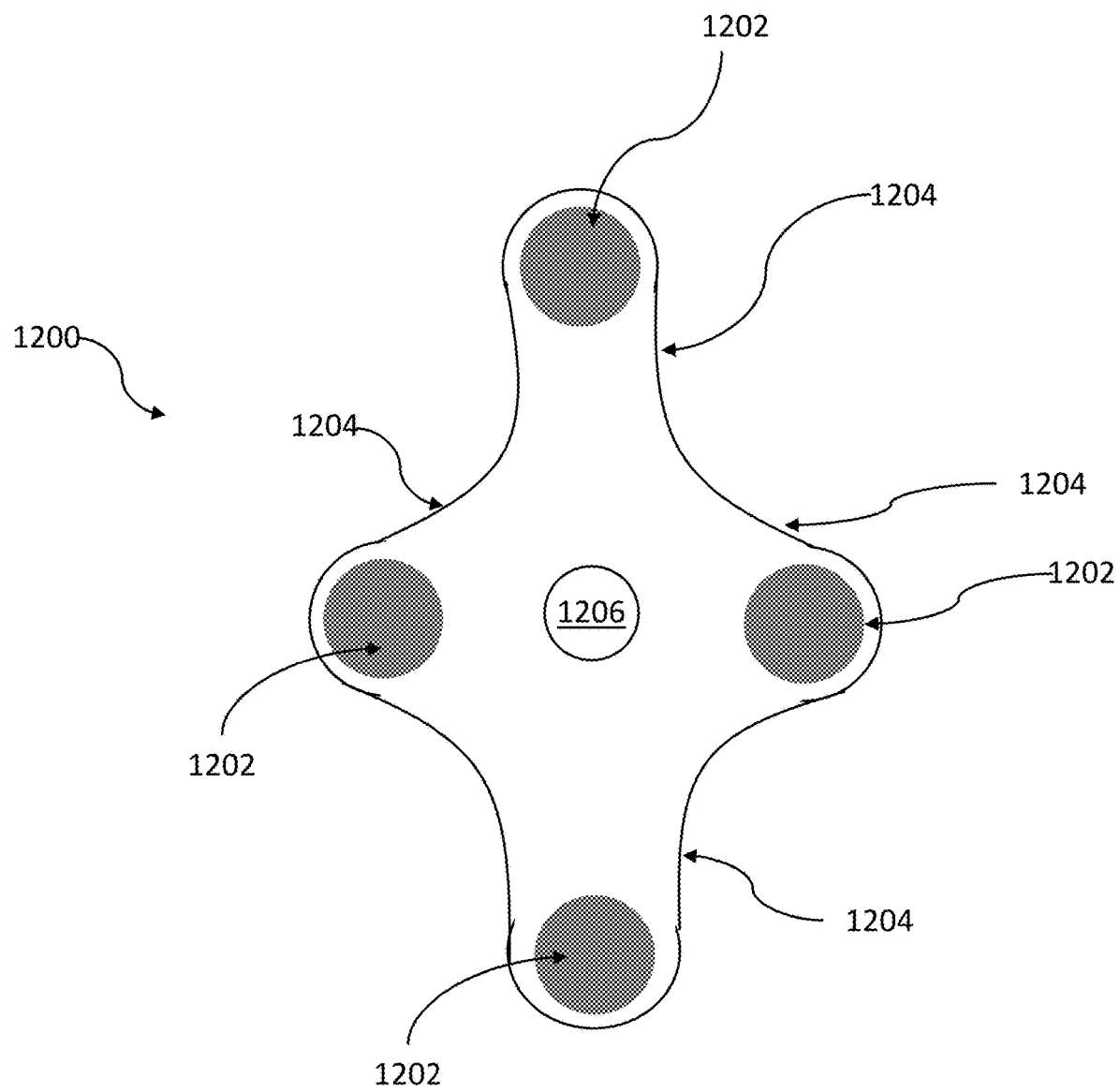
FIG. 12A is a top-view illustration of another embodiment of a flexible navigation array.

A variety of other embodiments are also possible for use of flexible navigation arrays. For example, flexible navigation arrays can include any number of navigation markers. The embodiment of FIG. 5 illustrates a flexible navigation array having three navigation markers, but flexible navigation arrays can be formed with a different number of navigation markers. For example, FIG. 12A illustrates another embodiment of a flexible navigation array 1200 having four navigation markers 1202. In other embodiments, any other number of navigation markers can be included. In some embodiments, a flexible navigation array can be created with up to about 20 navigation markers. In some embodiments, each navigation marker can be formed on an arm of flexible material (e.g., arm 1204 in FIG. 12A) extending from a central locating feature (e.g., feature 1206 in FIG. 12A).

Figure 12B:
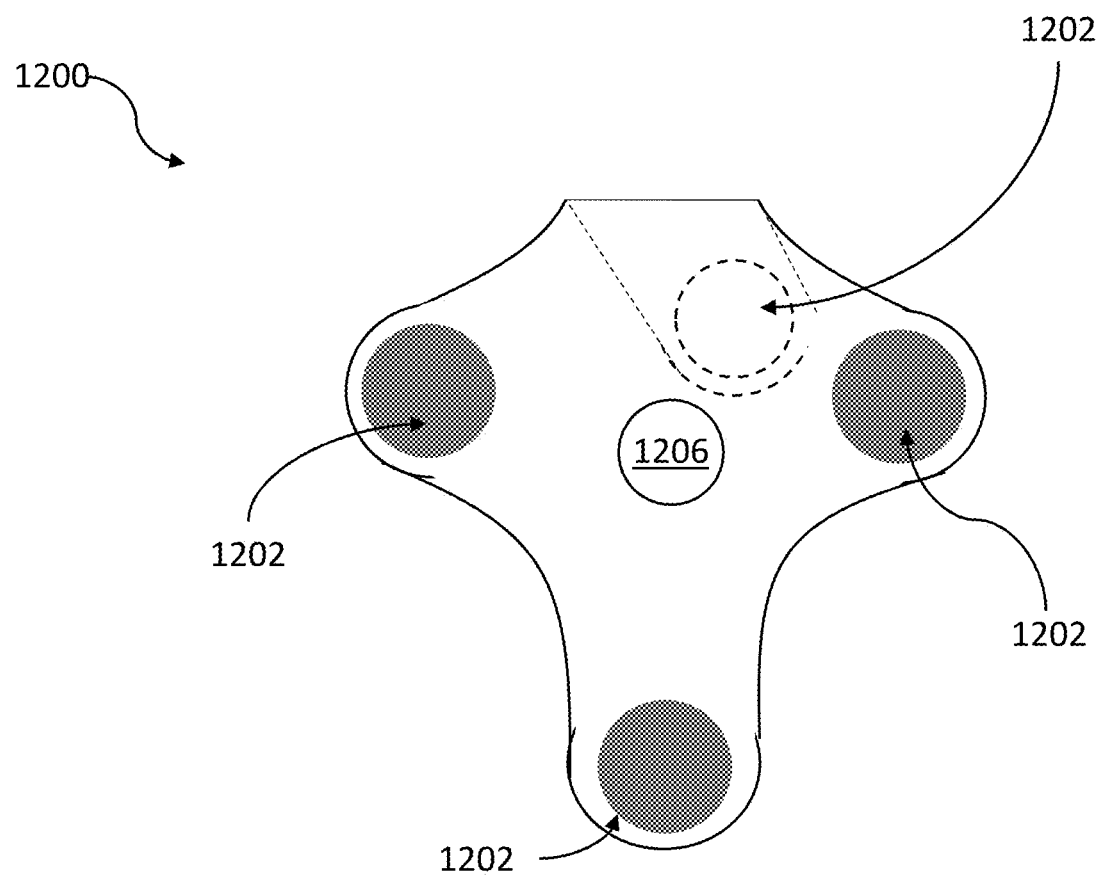
FIG. 12B is a top-view illustration the flexible navigation array of FIG. 12A with one navigation marker tucked behind the array.

In some embodiments, a flexible navigation array can include at least one more navigation marker than is necessary for operation of a CAS tracking system, such that an extra or spare navigation array is available for use in a particular situation, e.g., a portion of a procedure where an additional navigation marker is needed to change a digital ID of an array or provide additional motion tracking capability (e.g., tracking in an additional dimension or with additional precision). In such embodiments, any unnecessary navigation markers can be permanently removed or temporarily hidden from view of the CAS tracking system. Permanent removal can include, for example, cutting off a navigation marker and/or arm 1204 using shears or another cutting instrument. In some embodiments, any unnecessary navigation markers can be folded or tucked behind the remainder of the flexible navigation frame such that they are not visible to the CAS tracking system and do not interfere with use of the other navigation markers. FIG. 12B, for example, shows the four-marker flexible navigation array 1200 with the top marker 1202 shown in phantom because it is tucked behind the remainder of the body of the flexible navigation array.

Figure 13A:
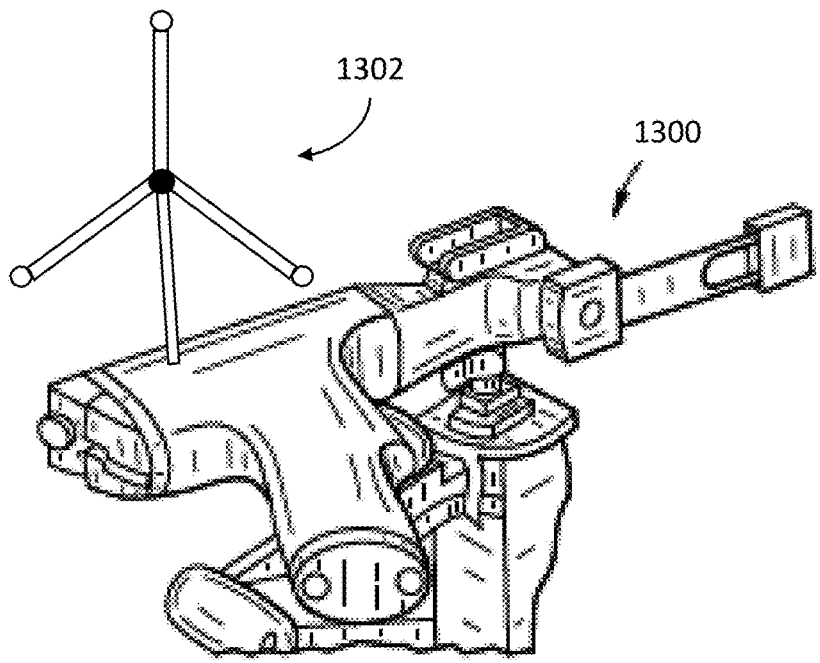
FIG. 13A is a perspective-view illustration of one embodiment of a surgical instrument including a rigid frame integrally formed into a body of the instrument.
Figure 13B:
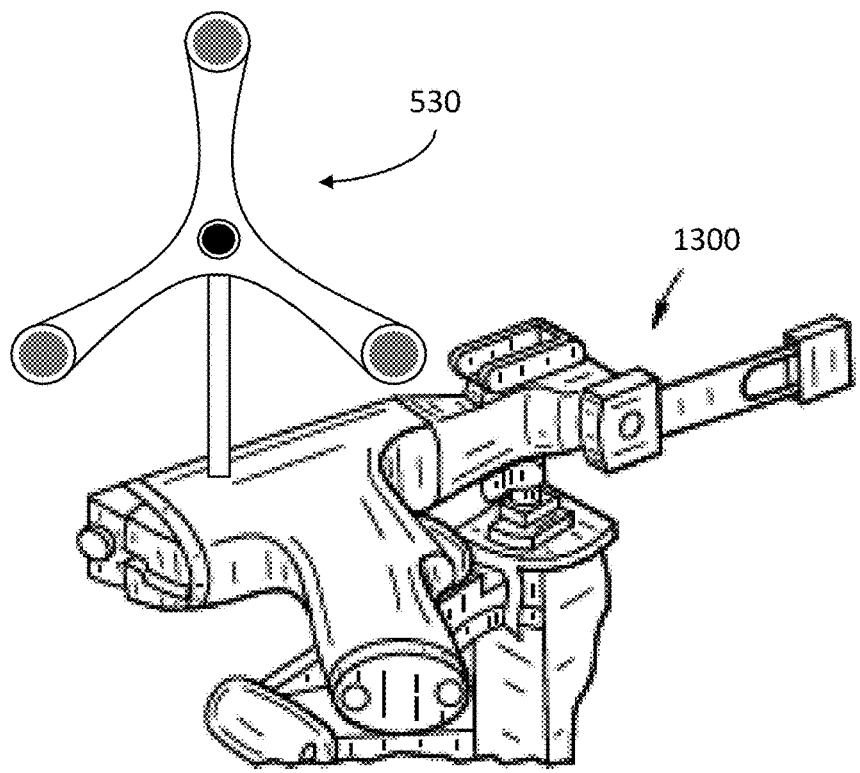
FIG. 13B is a perspective-view illustration of the surgical instrument of FIG. 13A with the flexible navigation array of FIG. 5A coupled to the rigid frame of the surgical instrument.

While the embodiments described above with respect to FIGS. 3A-5E illustrate use of a flexible navigation array with a modular rigid frame that in turn couples to a surgical instrument, in other embodiments a frame-like component can be integrally formed with the surgical instrument or an exterior surface of the instrument can include coupling locations or features formed thereon or therein to allow a flexible navigation array to couple directly to an outer surface of the instrument and eliminate the use of a frame or frame-like structure protruding from the surgical instrument. FIG. 13A illustrates one embodiment of a surgical instrument 1300 having a rigid frame-like structure 1302 integrally formed therewith to provide a rigid and permanent coupling with the remainder of the surgical instrument. The frame can include any of the various frame features described herein and can therefore couple with any of a variety of flexible navigation arrays. For example, FIG. 13B illustrates the surgical instrument 1300 with the flexible navigation array 530 coupled to the integral frame-like structure 1302 similar to how the array 530 is shown coupled to the frame 510 in FIG. 5E.

Figure 14A:
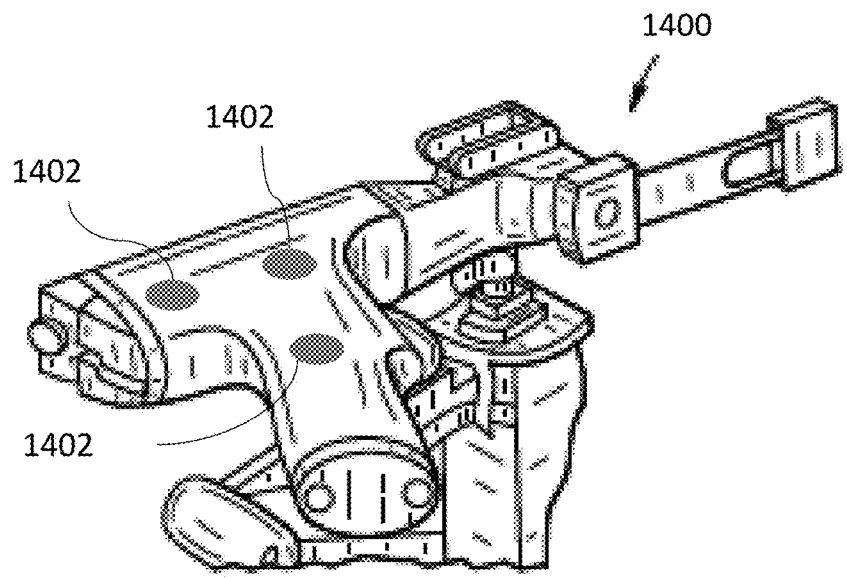
FIG. 14A is a perspective-view illustration of one embodiment of a surgical instrument including recesses formed in an outer surface thereof that are configured to receive portions of a flexible navigation array.
Figure 14B:
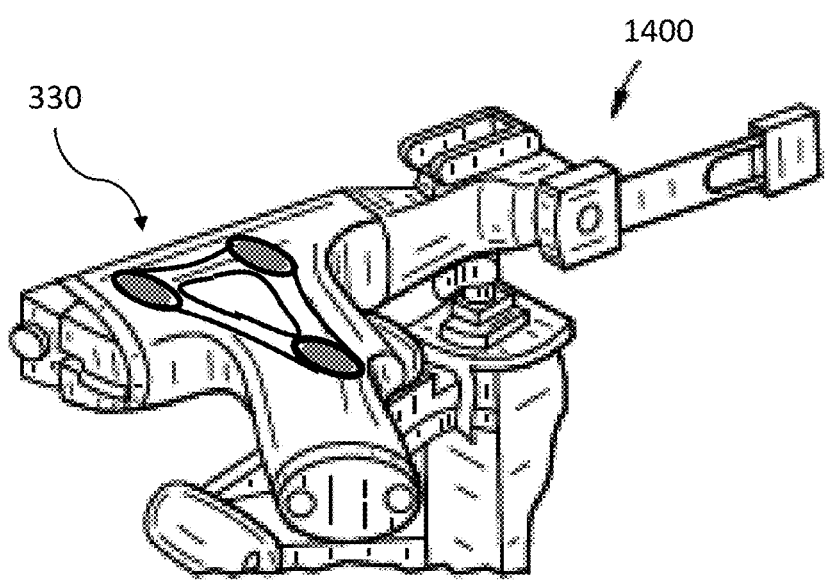
FIG. 14B is a perspective-view illustration of the surgical instrument of FIG. 14A with the flexible navigation array of FIG. 3A coupled to the surgical instrument.

In still other embodiments, an exterior surface of the surgical instrument can include a plurality of coupling locations or features formed thereon or therein to allow a flexible navigation array to couple directly to the exterior surface of the surgical instrument. FIG. 14A illustrates one embodiment of a surgical instrument 1400 that can include a plurality of coupling locations 1402 formed in an outer surface thereof. The coupling locations can include any of the various embodiments described herein, e.g., recesses, pins, rails, openings, etc. that can receive and retain a position of a navigation marker. FIG. 14B illustrates the surgical instrument 1400 with the flexible navigation array 330 coupled directly thereto without the use of a frame structure separate or protruding from the exterior surface of the instrument. In embodiments where coupling in this manner is possible, it can be possible to reduce cost and complexity while increasing accuracy by directly coupling the flexible navigation array to the instrument.

In some instances, the coupling locations 512 and coupling regions 532 together locate the rigid navigation markers 340 to within a tolerance of 0.1 mm or better with respect to each other and to the attachment arm 518. Locating the navigation markers with such precision and accuracy can aid optimum operation of the navigation system, as undesired movement of the navigation markers relative to the rigid frame (and instrument or other component being tracked to which the frame is rigidly attached) can impair the ability of the tracking unit 50 to accurately determine the position and orientation of the navigation array. Moreover, the use of a flexible navigation array coupled to a rigid frame or instrument can provide advantages over traditional rigidly-attached navigation arrays. For example, certain surgical instruments, such as oscillating saws, can product significant vibration during use. The vibration can be significant enough in some cases to case the tracking unit 50 and surgical navigation system to lose track of a navigation array due to the vibration of the navigation array markers. Embodiments according to the present disclosure can in some cases dampen the magnitude of vibration passed from the rigid frame or instrument to the navigation markers via the portions of the flexible arms or body disposed between the navigation markers and the rigid frame or instrument.

Figure 6A:
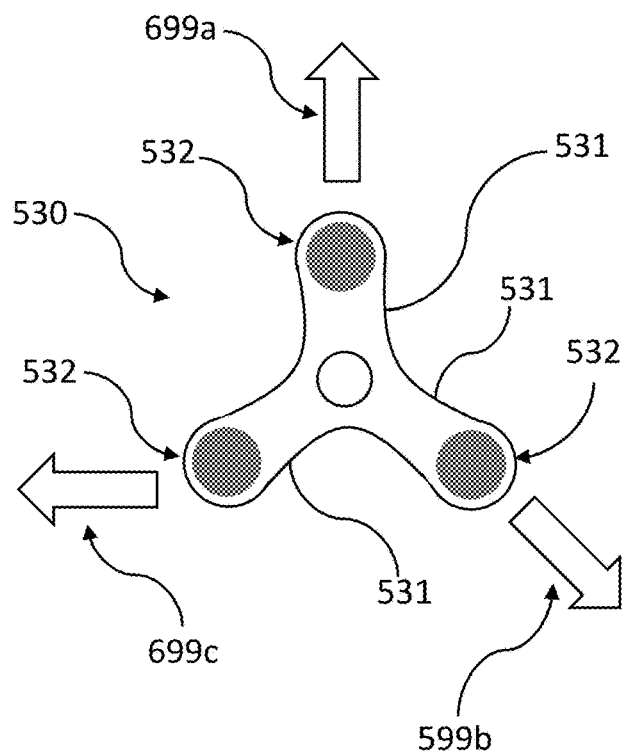
FIG. 6A is a top-view illustration of the embodiment of a flexible navigation array of FIG. 5A being stretched to fit a different rigid frame.
Figure 6B:
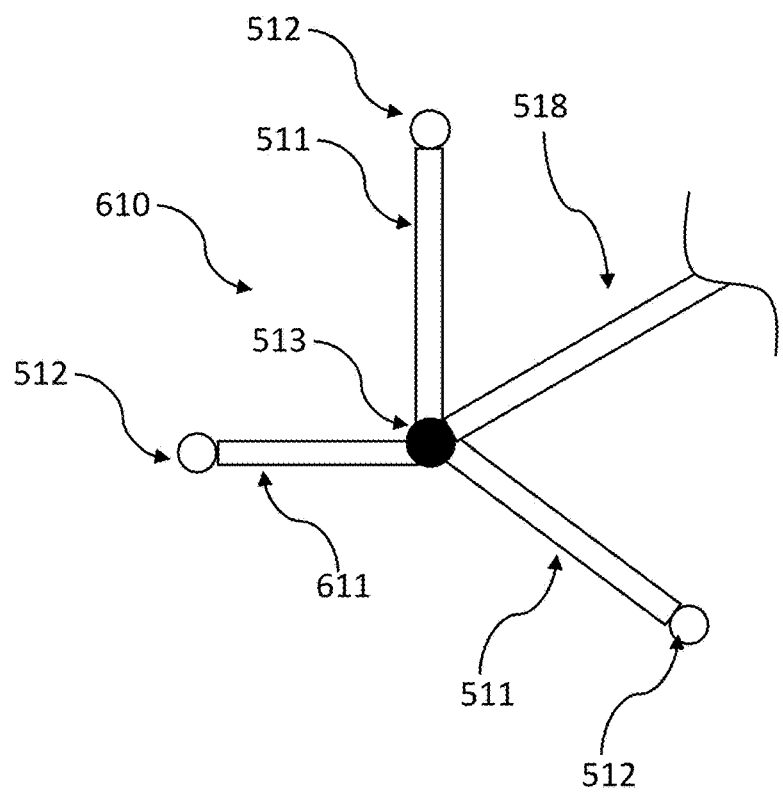
FIG. 6B is a top-view illustration of an embodiment of another rigid frame for holding a flexible navigation array.
Figure 6C:
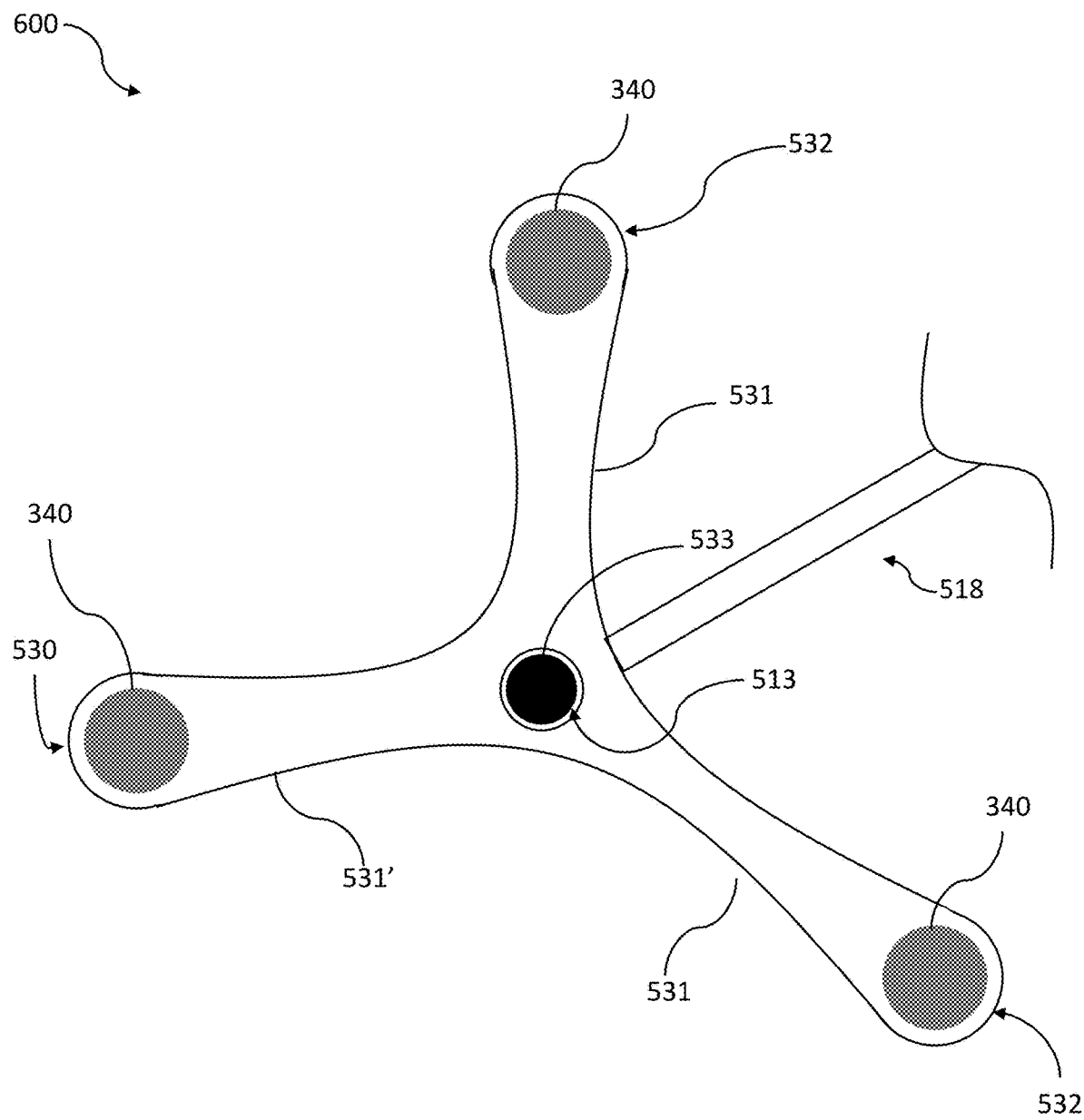
FIG. 6C is a top-view illustration of the flexible navigation array embodiment of FIG. 5A coupled with the rigid frame embodiment of FIG. 6B.

Due to the deformable nature of the flexible navigation array 530, the same flexible navigation array 530 can be coupled to a variety of different sizes and shapes of rigid frames or instruments. For example, FIG. 6A is an illustration of the embodiment of the flexible navigation array 530 being stretched to fit a different rigid frame 610, which is shown in FIG. 6B. In FIG. 6A, the flexible navigation array 530 is stretched in three directions 699a-699c that are determined by the shape of the rigid frame 610 shown in FIG. 6B. FIG. 6B is an illustration of the rigid frame 610, showing one arm 611 that, as compared with the rigid frame of FIG. 5B, has a different length and orientation with respect to the other arms 511. Accordingly, FIG. 6C is an illustration of the flexible navigation array 530 coupled with the rigid frame 610 in the new orientation as defined by the change in the configuration of the arm 611.

These features of the flexible navigation array can allow a variably-configurable system using a single flexible array component. For example, a single flexible navigation array can be produced having a maximum desired number of navigation markers, e.g., at least two to identify an axis in three-dimensional space, at least three to fix a position and orientation in three-dimensional space, and up to twenty or more. For example, FIG. 12A illustrates one embodiment of a flexible navigation array 1200 having four navigation markers 1202, but different numbers are also possible. Whatever the number of navigation markers included, this single flexible navigation array can be mass produced and distributed in connection with a series of rigid frames or instruments having unique geometries and/or number of coupling locations. In preparation for a procedure, a user can pick one of the rigid frames to couple to an instrument or component to be tracked, or can pick an instrument having features configured to couple to the flexible navigation array directly, as well as one of the flexible navigation arrays. The flexible navigation array can be stretched over and coupled to the rigid frame or instrument to position a navigation marker at each coupling location of the frame or instrument. Additional, unused navigation markers can be tucked between the frame and flexible navigation array such that they are not visible to the tracking unit 50, as shown in FIG. 12B, or cut off from the flexible navigation array and discarded. In this manner, a user can simultaneously track many devices in a surgical field using a single type of disposable flexible navigation array. Indeed, in some embodiments, an operating room or other surgical prep area can include a dispenser that holds, e.g., several stacked flexible navigation arrays for easy access when setting up an instrument or other component for navigated use during a surgical procedure.

Figure 7A:
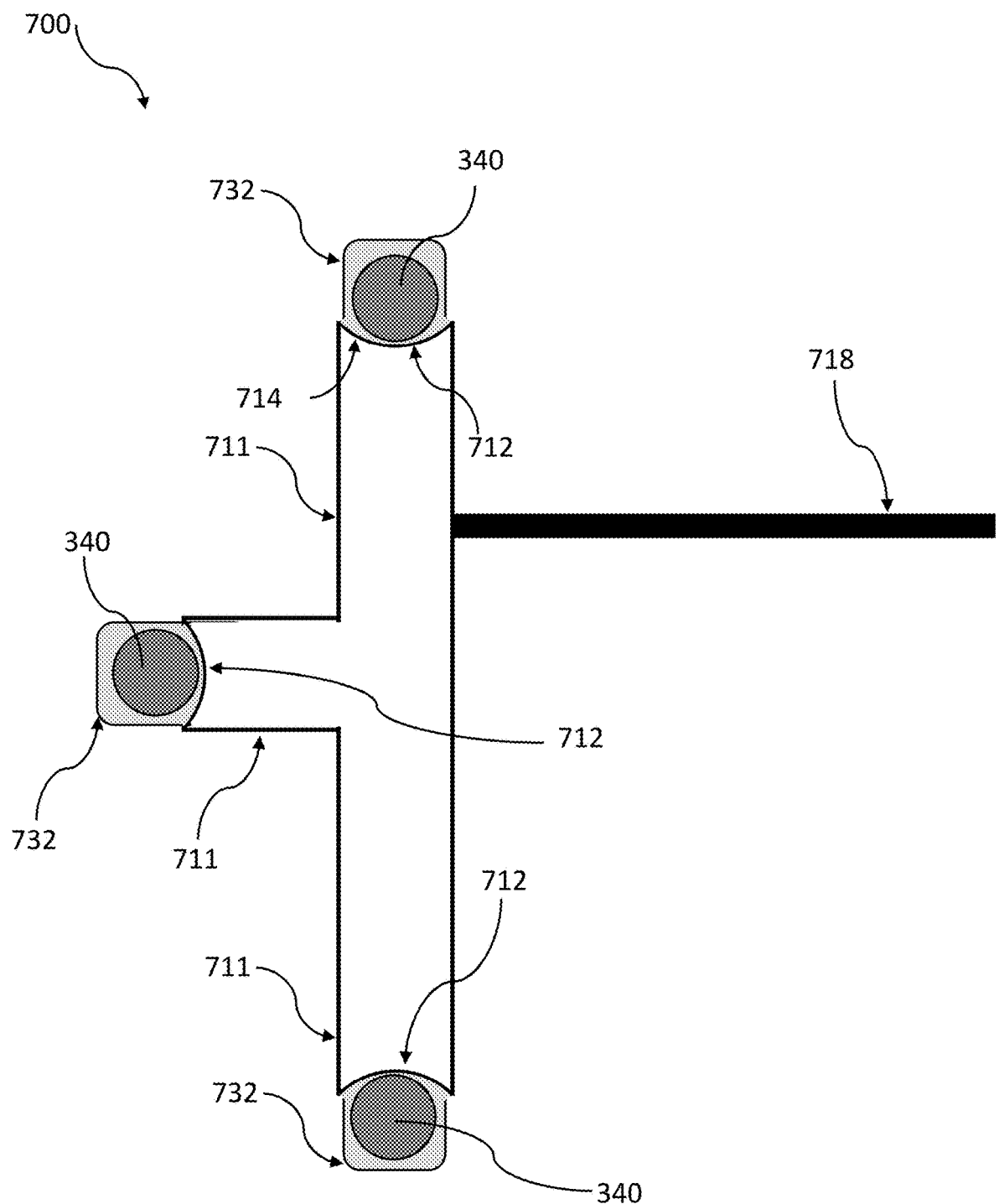
FIG. 7A is a top-view illustration of another flexible navigation array embodiment coupled with a rigid frame embodiment having a channel construction.
Figure 7B:
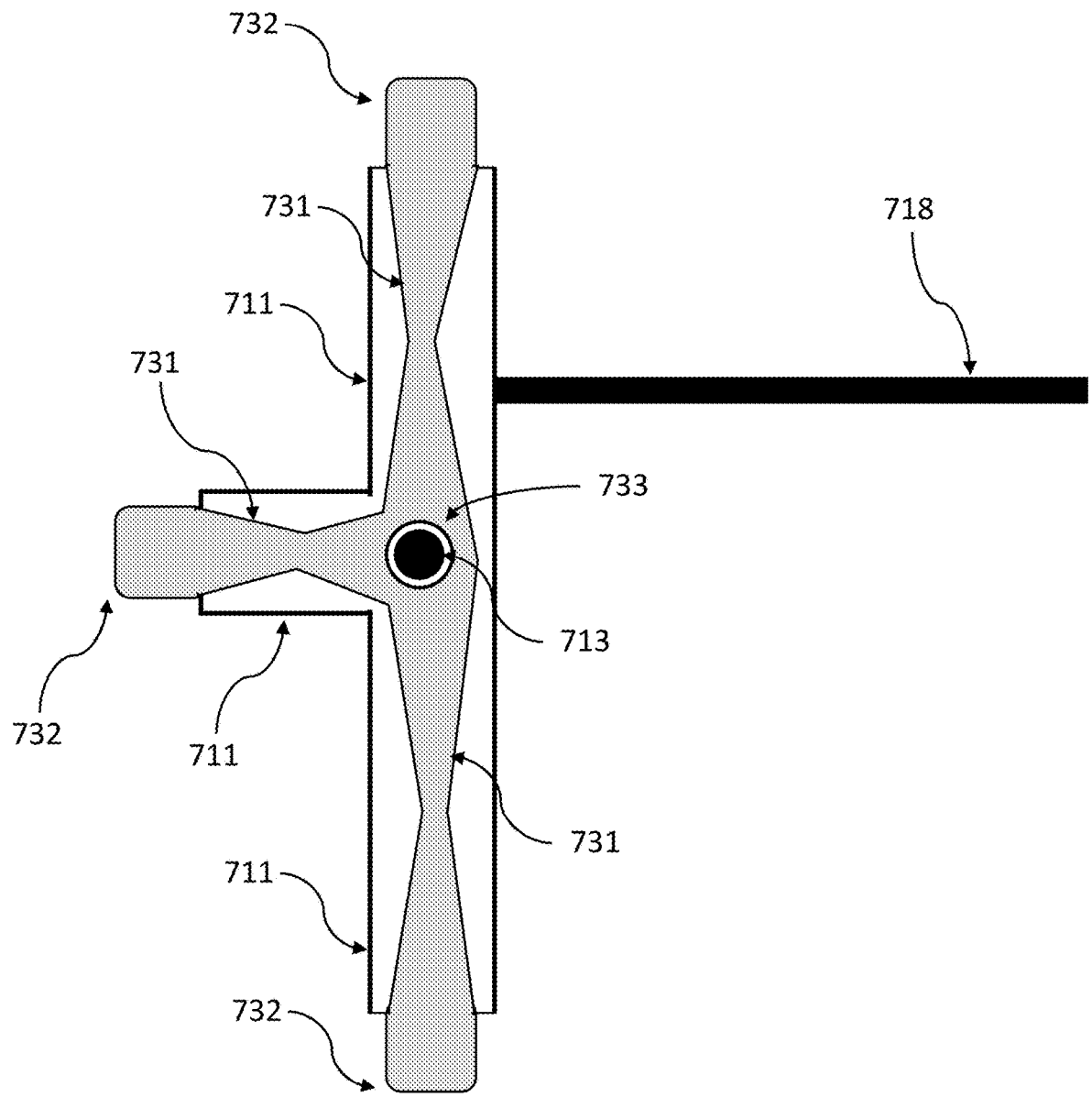
FIG. 7B is a bottom-view illustration of the embodiment of FIG. 7A.

FIGS. 7A and 7B are illustrations of a surgical navigation array 700 including another flexible navigation array 730 embodiment coupled with a rigid frame 710 embodiment having a channel construction. FIG. 7A shows a top-view of the rigid frame 710, which includes arms 711 extending in a T-shape and an attachment arm 718 extending from one arm 711 of the rigid frame. Each arm 711 of the rigid frame 710 has a channel cross-section, such that the majority of each arm 731 of the flexible navigation array 730 is disposed in the channel of the respective arm 711, as shown in FIG. 7B. Returning to FIG. 7A, a coupling region 732 of each arm 731 of the flexible navigation array 730 includes a rigid navigation marker 340 and the integration of the flexible navigation array 730 with the rigid frame 710 positions each rigid navigation marker 340 at a terminal end 712 of each arm 711. In this manner, with each rigid navigation marker 340 can be held in position at the terminal end 712 of each arm 711 by a combination of the restoring force of each arm 731 urging the rigid navigation marker 340 and/or the coupling region 732 against the terminal end 712 of the arm 711 and the terminal end 712 of each arm 711 being sized and shape to hold and/or secure the rigid navigation marker 340 and/or the coupling region 732 in place. For example, the terminal end 712 of each arm 711 can be curved or concave in shape, as shown at arrow 714, to help centrally position the navigation marker 340 relative to a central longitudinal axis of the arm 711. FIG. 7B shows the underside of the rigid frame 710, with the arms 731 of the flexible navigation array 730 disposed in the channels of each arm 711 of the rigid frame, as shown in more detail in FIGS. 7C-7E. FIG. 7B also shows that the flexible navigation array 730 includes a central opening 733 that is disposed around a central protruding feature, such as an attachment peg 713 (extending out of the plane of the page in FIG. 7B), located at the intersection of the arms 711 of the rigid frame 710.

Figure 7C:
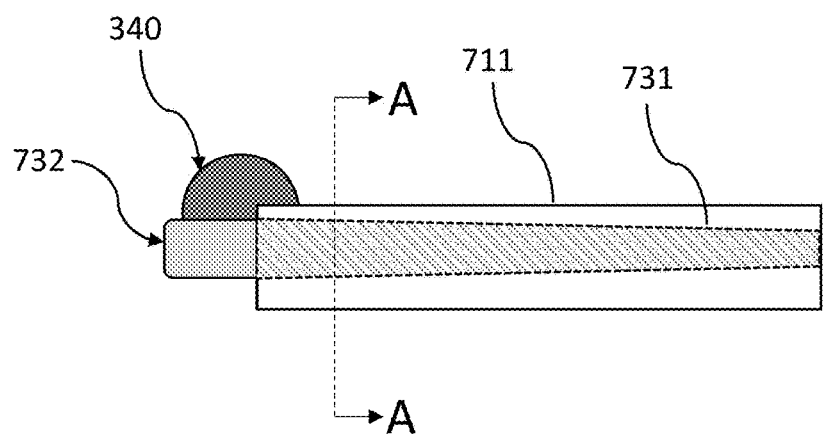
FIG. 7C is a side view illustration of the flexible navigation array and rigid frame embodiments of FIGS. 7A and 7B showing the coupling between the flexible navigation array and the rigid frame.
Figure 7D:
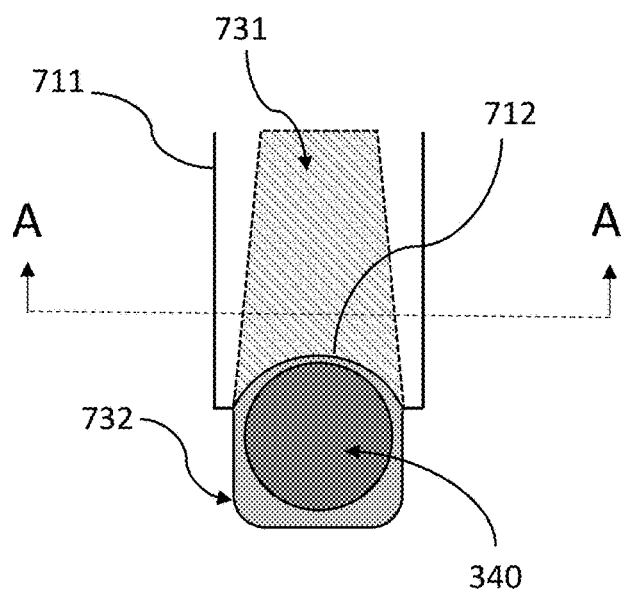
FIG. 7D is a top view illustration of the flexible navigation array and rigid frame embodiments of FIGS. 7A and 7B showing the coupling between the flexible navigation array and the rigid frame.
Figure 7E:
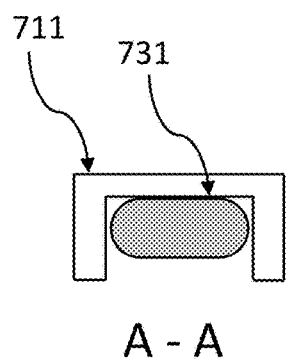
FIG. 7E is a cross-sectional-view illustration of the flexible navigation array and rigid frame embodiments of FIGS. 7A and 7B taken along the line A-A in FIGS. 7C and 7D.

FIGS. 7C-7E are detail illustrations of the flexible navigation array 730 and rigid frame 710 showing the coupling between the rigid navigation marker 340 and/or the coupling region 732 and the terminal end 712 of each arm 711. FIG. 7C shows a side view of one arm 711, with the arm 731 of the flexible navigation array 730 visible inside the channel of the arm 711. FIG. 7D is a top-down detail view of the engagement between the terminal end 712 of the arm 711 and the rigid navigation marker 340. FIG. 7E is a cross-section of location A-A in FIGS. 7C and 7D.

Figure 8:
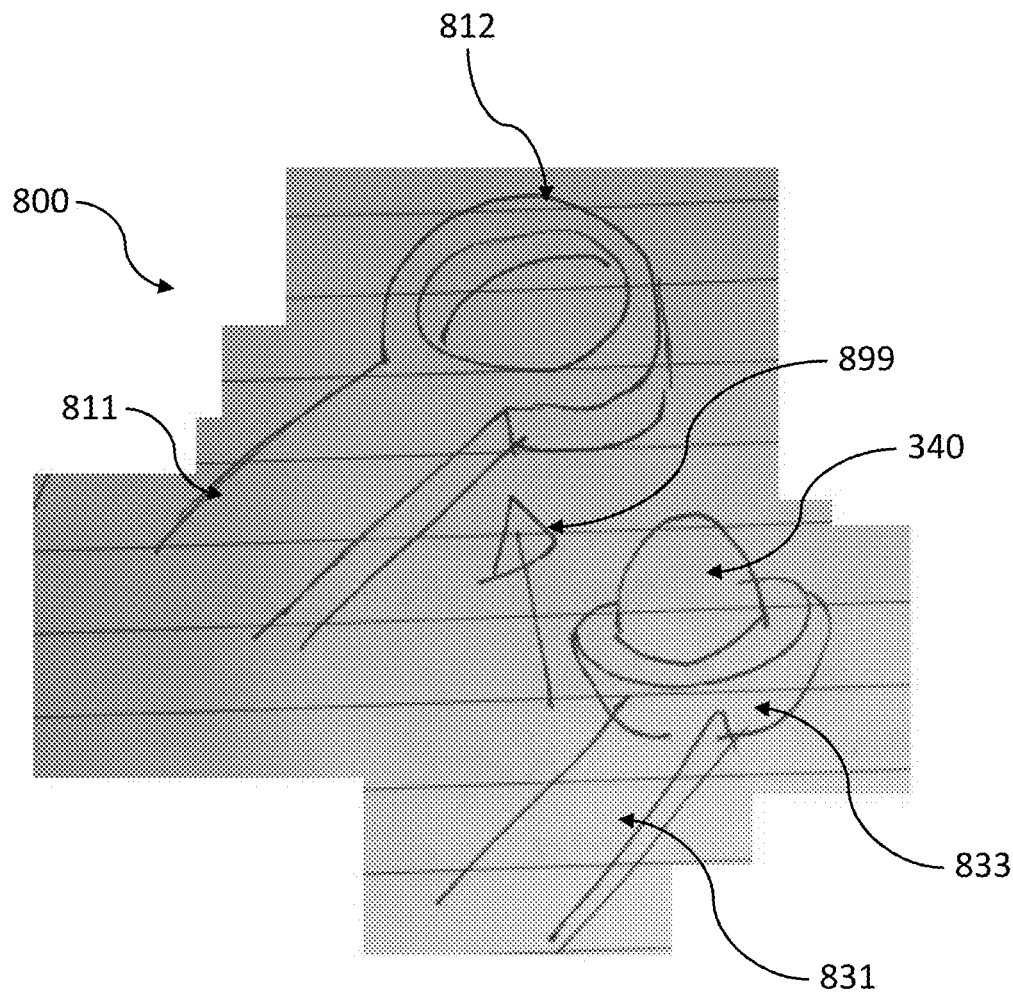
FIG. 8 is a perspective-view illustration of a coupling arrangement between a flexible navigation array and a rigid frame.

FIG. 8 is an illustration of another coupling arrangement between a flexible navigation array and a rigid frame, which includes a different type of engagement between a coupling region 833 of a flexible navigation array and a coupling location 812 of a rigid frame. The coupling location 812 includes a hoop or loop-shaped region that is configured to receive the rigid navigation marker 340 therethrough and the flexible arm 831 of the flexible navigation array includes a coupling region 833 that is sized and shaped to mate with the coupling location 812. The navigation marker 340 and/or coupling region 833 can interface with the coupling location 812 using a variety of methods, including an interference fit or any of a variety of interacting and complementary features (e.g., protrusions and recesses, etc.).

Figure 9:
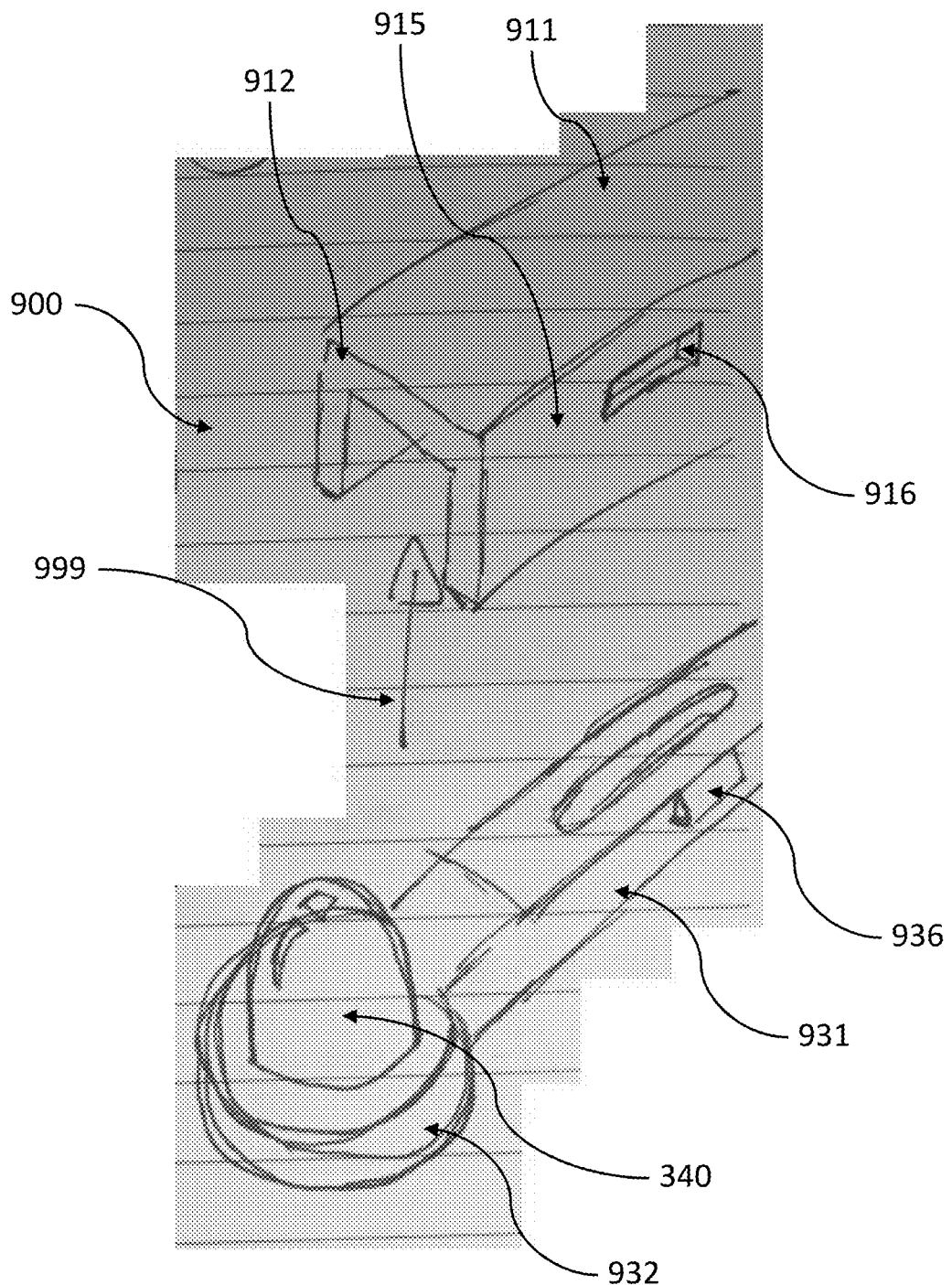
FIG. 9 is a perspective-view illustration of another coupling arrangement between a flexible navigation array and a rigid frame.

FIG. 9 is an illustration of another coupling arrangement between a flexible navigation array and a rigid frame. In FIG. 9, an arm 911 of a rigid frame is shown to have a channel for receiving an arm 931 of a flexible navigation array. A terminal end 912 of the arm 911 is configured to receive the rigid navigation marker 340 and/or a coupling region 932 to secure the flexible navigation array to the rigid body having the arm 911. Additionally, one or both sidewalls 915 of the arm 911 include an additional retention feature, such as a slot or recess 916 configured to receive a corresponding protrusion 936 on a side of the arm 931.

Figure 10A:
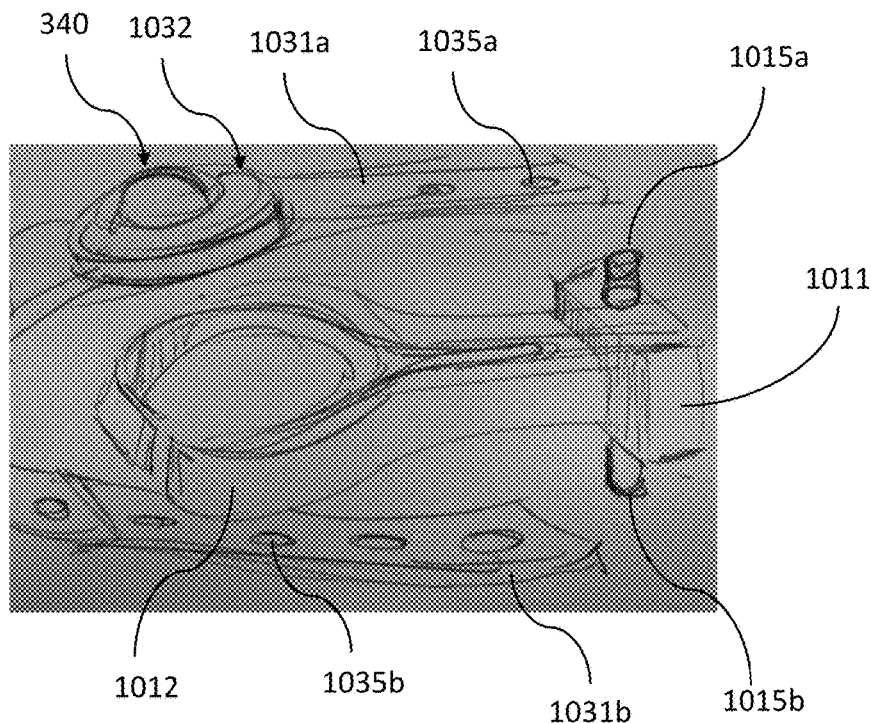
FIG. 10A is a perspective-view illustration of another coupling arrangement between a flexible navigation array and a rigid frame.
Figure 10B:
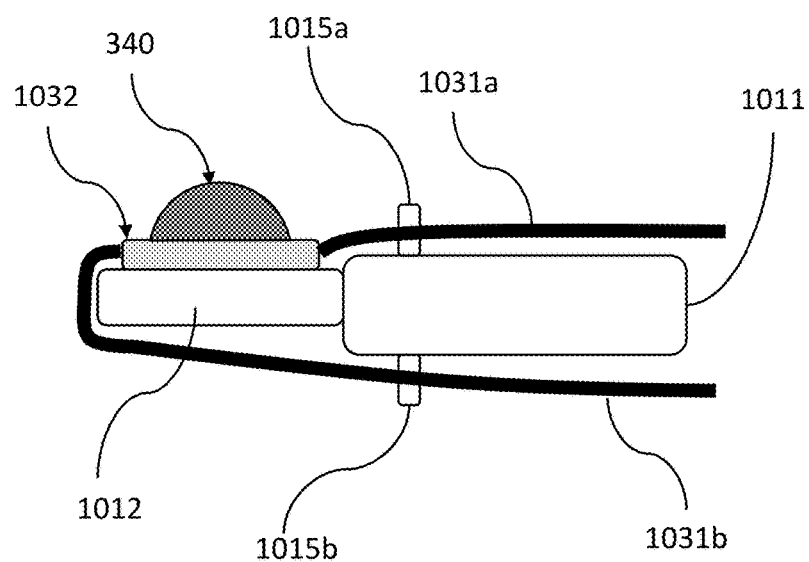
FIG. 10B is a side-view illustration of the embodiment of FIG. 10A.

FIGS. 10A and 10B are illustrations of yet another coupling arrangement between a flexible navigation array and a rigid frame. FIG. 10A shows an arm 1011 of a rigid frame having a coupling location 1012 arranged as a hoop that is configured to receive a coupling location 1032 of a flexible navigation array. The arm 1011 includes pins 1015a, 1015b extending from opposite sides of the arm 1011 adjacent to the coupling location 1012. The flexible navigation array includes straps 1031a, 1031b extending from opposite sides of the coupling region 1032, with each strap 1031a, 1031b including holes 1035a, 1035b for engagement with the pins 1015a, 1015b to secure the coupling region 1032 and attached rigid navigation maker 340 to the coupling location 1012, as show in FIG. 10B. FIG. 10B is a side-view of the coupling region 1032 secured to the coupling location 1012 by each strap 1031a, 1031b being stretched and secured to the corresponding pin 1015a, 1015b on the arm 1011 of the rigid frame.

The above-described example embodiments are not the only ways a navigation marker can be coupled to a frame. Further details on other methods for coupling a navigation marker to a frame are disclosed in a U.S. patent application entitled "Systems and Methods for Coupling Navigation Markers to an Array," filed on a same date as this application, the entire contents of which are incorporated by reference herein. Still further, in some embodiments any of the above-described geometries of a rigid frame can be integrally formed into a surgical instrument to allow a flexible navigation array to be coupled directly to the instrument. For example, a frame having the above-described geometries can be integrally formed with a surgical instrument, as shown in FIG. 13A, or an exterior surface of the instrument can include individual coupling locations or features formed in the surface, as shown in FIG. 14A. In certain embodiments, any of the above-described frame geometries or coupling mechanisms can be integrated into an integrally-formed frame that is part of a surgical instrument or an exterior surface of the instrument.

Figure 11A:
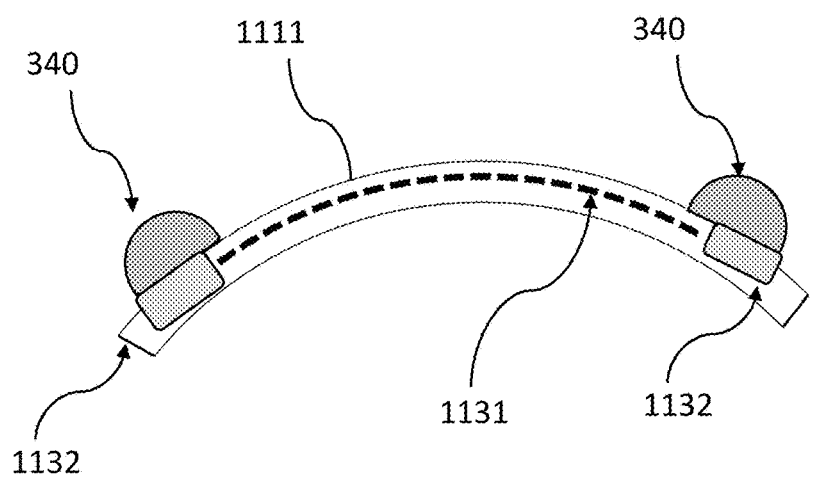
FIG. 11A is a side-view illustration of a flexible navigation array disposed on and a rigid frame in a non-planar arrangement.
Figure 11B:
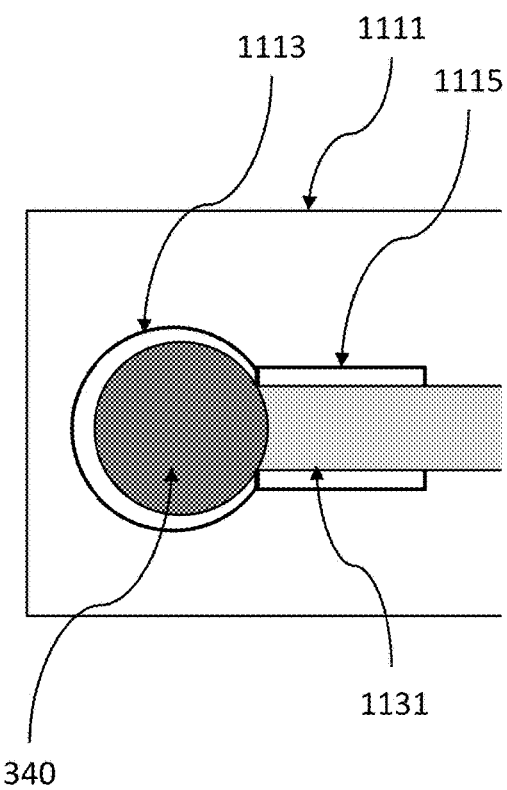
FIG. 11B is a top-view detail illustration of the embodiment of FIG. 11A.

FIGS. 11A and 11B are illustrations of a flexible navigation array disposed on a rigid frame 1111 in a non-planar arrangement. FIG. 11A shows a side-view of a rigid frame 1111 with a curved shape. A flexible navigation array is disposed on the rigid frame 1111 such that coupling regions 1132 of each arm 1131 are attached to the rigid frame via recesses 1113, 1115 in the surface of the rigid frame 1111, as shown in more detail in FIG. 11B. The frame 1111 includes a coupling recess 1113 configured to receive the coupling region 1132 and rigid navigation marker 340 of the flexible navigation array and the rigid frame can further include a recess 1115 in which all or a portion of each arm 1131 extending from the coupling region 1132 can be disposed. The shape of the coupling recess 1113 can hold the coupling region 1132 and/or rigid coupling marker 340 in place against the surface of the rigid frame 1111 and allow the arms 1131 of the flexible navigation array to be stretched against the rigid frame 1111 to allow each coupling region 1132 to be disposed in a corresponding coupling recess 1113. In other embodiments, the above-described principles of the frame 1111 can be utilized to facilitate formation of coupling recesses 1113 into an exterior surface of a surgical instrument, e.g., as shown in FIG. 14A. Such a configuration can allow a flexible navigation array to be coupled directly to an outer surface of the surgical instrument, as shown in FIG. 14B, without the need for a separate rigid frame. This can potentially provide cost savings, complexity reductions, and improved accuracy by coupling the navigation markers directly to the instrument rather than coupling to an intermediate frame component.

The devices, systems, and methods disclosed herein can be used in minimally-invasive surgery and/or open surgery. As noted above, any of a variety of surgical procedures can be performed utilizing the surgical navigation trackers described herein, including various orthopedic procedures, such as knee surgery, spine surgery, shoulder surgery, hip surgery, etc. While the devices and methods disclosed herein are generally described in the context of orthopedic surgery on a human patient, it will be appreciated that the methods and devices disclosed herein can be used in any of a variety of surgical procedures with any human or animal subject, or in non-surgical procedures.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely example embodiments, various other methods that include additional steps or include fewer steps are also within the scope of the present disclosure.

The instruments, devices, and systems disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, silicones, rubbers, and so forth. The various components of the instruments disclosed herein can have varying degrees of rigidity or flexibility, as appropriate for their use. Device sizes can also vary greatly, depending on the intended use and surgical site anatomy. Furthermore, particular components can be formed from a different material than other components. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning of a device can utilize a variety of techniques for disassembly, cleaning/replacement, and reassembly. Use of such techniques, and the resulting reconditioned device, are all within the scope of the present disclosure.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

The embodiments of the present disclosure described above are intended to be examples; numerous variations and modifications are possible and within the scope of this disclosure. Accordingly, the disclosure is not to be limited by what has been particularly shown and described. All publications and references cited herein are expressly incorporated by reference in their entirety.

What is claimed is:

1. A flexible marker system for use with a computer-assisted surgical (CAS) tracking system, comprising:
   a rigid frame or instrument defining a plurality of coupling locations each configured to position a navigation marker in a predetermined position; and
   a flexible array configured to be coupled with the rigid frame or instrument, the flexible array comprising an elastically deformable body and a plurality of navigation markers;
   wherein the flexible array is configured to be coupled to the rigid frame or instrument by stretching the elastically deformable body over the rigid frame such that each of the plurality of navigation markers is positioned at one of the plurality of coupling locations of the rigid frame or instrument.

2. The system of claim 1, wherein each of the plurality of navigation markers is rigid.

3. The system of claim 1,
   wherein the rigid frame or instrument comprises a plurality of channel sections, each channel section having one of the plurality of coupling locations; and
   wherein a portion of the elastically deformable body is configured to be received in each of the plurality of channel sections when the flexible array is coupled with the rigid frame or instrument.

4. The system of claim 1,
   wherein the rigid frame or instrument defines a central locating feature;
   wherein the elastically deformable body of the flexible array defines a corresponding central locating feature and a plurality of appendages extending therefrom; and
   wherein the central locating feature of the rigid frame or instrument is configured to retain the corresponding central locating feature of the flexible array such that each of the plurality of appendages is configured to be held in an elastically deformed configuration extending between the central locating feature of the rigid frame or instrument and a one of the plurality of coupling locations.

5. The system of claim 1,
   wherein the rigid frame or instrument comprises a surface, the surface having formed therein a recess defining one of the plurality of coupling locations; and
   wherein the at least a portion of the elastically deformable body of the flexible array is configured to be stretched across the surface when the flexible array is coupled with the rigid frame or instrument.

6. The system of claim 1,
   wherein at least one of the coupling locations comprises a coupling hook feature; and
   wherein the flexible array includes a loop feature that is configured to interface with the coupling hook feature to secure the flexible array to the rigid frame or instrument.

7. The system of claim 1,
   wherein at least one of the coupling locations comprises a recess; and
   wherein the flexible array includes a protrusion that is configured to be received and retained by the recess when the flexible array is coupled with the rigid frame or instrument.

8. The system of claim 1,
wherein at least one of the coupling locations comprises a pin; and
wherein the flexible array includes a strap with holes that is configured to be received and retained by the pin when the flexible array is coupled with the rigid frame or instrument.

9. The system of claim 1,
wherein at least one of the coupling locations comprises a first pin on a first side of the rigid frame or instrument and a second pin on a second side of the rigid frame or instrument opposite the first side;
wherein the flexible array includes first and second strap portions with at least one of the plurality of navigation markers disposed between the first and second strap portions; and
wherein the first and second strap portions each define one or more holes configured to receive the first and second pins, respectively, when the flexible array is coupled with the rigid frame or instrument.

10. The system of claim 1,
wherein at least one of the coupling locations defines a curved surface; and
wherein the flexible array includes a first side having at least one of the plurality of navigation markers and a second side, opposite the first side, configured to interface with the curved surface of the coupling location when the flexible array is coupled with the rigid frame or instrument.

11. The system of claim 1, wherein each of the plurality of navigation markers is configured to be located in space using stereoscopic sensors that detect light reflected or emitted from the plurality of navigation markers.

12. The system of claim 11, wherein each of the plurality of navigation markers comprises an optical lens device configured to reflect infra-red light.

13. The system of claim 1,
wherein the rigid frame or instrument comprises a channel section; and
wherein a portion of the elastically deformable body is configured to be received in the channel section when the flexible array is coupled with the rigid frame or instrument.

14. The system of claim 13,
wherein the channel section defines an end surface and the end surface comprises one of the plurality of coupling locations such that an elastic restoration force of the elastically deformable body maintains a position of at least one of the plurality of navigation markers relative to the end surface when the flexible array is coupled with the rigid frame or instrument.

15. The system of claim 1,
wherein the rigid frame or instrument comprises a plurality of arms;
wherein each of the plurality of arms comprises a respective one of the plurality of coupling locations; and
wherein a portion of the elastically deformable body is configured to be elastically deformed along each of the plurality of arms when the flexible array is coupled with the rigid frame or instrument.

16. The system of claim 15, wherein each of the plurality of arms extends from a central location.

17. The system of claim 15, wherein the elastically deformable body comprises a plurality of arm sections configured to extend along a corresponding one of the plurality of arms when the flexible array is coupled with the rigid frame or instrument.

18. The system of claim 15,
wherein at least one of the plurality of arms defines channel section; and
wherein the elastically deformable body comprises an arm section configured to be received in the channel section when the flexible array is coupled with the rigid frame or instrument.

19. A flexible marker for use with a computer-assisted surgical (CAS) tracking system, the flexible marker comprising:
an elastically deformable flexible body;
a plurality of rigid navigation markers configured to be detected by a CAS tracking system;
wherein the elastically deformable flexible body is configured to be stretched over a rigid frame or instrument in order to position the plurality of rigid navigation markers at specific positions relative to the rigid frame or instrument.

20. The flexible marker of claim 19, wherein each of the plurality of rigid navigation markers comprises a rigid hemisphere portion.

21. The flexible marker of claim 19, wherein each of the plurality of rigid navigation markers is configured to reflect infra-red light.

22. The flexible marker of claim 19, wherein the elastically deformable flexible body has a plurality of appendages, each containing one of the plurality of rigid navigation markers.

23. The flexible marker of claim 19, wherein the plurality of rigid navigation markers includes at least three rigid navigation markers.

24. The flexible marker of claim 19, wherein the plurality of rigid navigation markers includes at least four rigid navigation markers.

25. A surgical method, comprising:
positioning a rigid frame or instrument relative to an object to be tracked by a computer-assisted surgical (CAS) tracking system; and
elastically deforming a body of a flexible array over the rigid frame or instrument and positioning a plurality of navigation markers of the flexible array at coupling locations of the rigid frame or instrument.

26. The method of claim 25, comprising:
disposing a portion of the body in a channel of the rigid frame or instrument such that a coupling region at an end of the channel secures one of the plurality of navigation markers and retains the body in an elastically deformed position.

27. The method of claim 25, wherein each of the plurality of navigation markers comprises an optical lens device configured to reflect infra-red light.

28. The method of claim 25, wherein elastically deforming the body of the flexible array comprises elastically deforming a plurality of appendages of the body, each containing one of the plurality of navigation markers.

29. The method of claim 25, further comprising any of removing or hiding at least one of the plurality of navigation markers of the flexible array from view of the computer-assisted surgical tracing system.

30. The method of claim 25, comprising:
elastically deforming a first strap of the body and coupling the first strap to a retention feature on a first side of the rigid frame or instrument.

31. The method of claim 30, comprising:
 elastically deforming a second strap of the body and coupling the second strap to a retention feature on a second side of the rigid frame or instrument.

\* \* \* \* \*